(12) United States Patent
Carstens

(10) Patent No.: US 6,696,278 B1
(45) Date of Patent: Feb. 24, 2004

(54) METHOD FOR TRANSFER OF DNA SEGMENTS

(75) Inventor: Carsten-Peter Carstens, LaJolla, CA (US)

(73) Assignee: Stratagene, La Jolla, CA (US)

( * ) Notice: Subject to any disclaimer, the term of this patent is extended or adjusted under 35 U.S.C. 154(b) by 0 days.

(21) Appl. No.: 09/793,372

(22) Filed: Feb. 26, 2001

(51) Int. Cl.[7] .................. C12N 15/64; C12N 15/66; C12N 15/09; C12Q 1/68; C07H 21/04

(52) U.S. Cl. ..................... 435/91.4; 435/6; 435/29; 435/252.3; 435/252.33; 435/320.1; 435/325; 435/91.1; 435/91.41; 435/91.42; 435/471; 435/472; 435/440; 536/23.1

(58) Field of Search .................. 435/6, 29, 320.1, 435/252.3, 440, 325, 471, 472, 91.1, 91.4, 91.41, 252.33, 91.42; 536/23.1

(56) References Cited

U.S. PATENT DOCUMENTS 5,888,732 A * 3/1999 Hartley et al. ................ 435/6
6,156,509 A   12/2000 Schellenberger

OTHER PUBLICATIONS

Goetz, et al. The Journal of Biological Chemistry, 1988, vol. 263, No. 31, pp. 16443–16451.*

Hoflack, et al. (1997). "Nucleotide Sequence and Characterization of the Cryptic *Bacillus thuringiensis* Plasmid pGI3 Reveal a New Family if Rolling Circle Replicons," vol. 179, No. 16, pp. 5000–5008.

* cited by examiner

Primary Examiner—Gerald G. Leffers, Jr.
(74) Attorney, Agent, or Firm—Palmer & Dodge LLP; Kathleen M. Williams

(57) ABSTRACT

The present invention provides a method of transfer of a gene of interest from a first vector to a product vector comprising contacting a first and second vector in vitro with a site-specific recombinase so as to generate a co-integrate vector comprising the components of the first and second vector, and introducing the co-integrate vector to a prokaryotic host cell so as to generate a product vector by rolling circle replication, comprising the gene of interest.

8 Claims, 5 Drawing Sheets

Adapted from Kronberg and Baker, DNA Replication, 2nd Ed. 1992

FIG. 5A

CTAAATTGTAAGCGTTAATATTTTGTTAAAATTCGCGTTAAATTTTTGTTAAATCAGC
TCATTTTTTAACCAATAGGCCGAAATCGGCAAAATCCCTTATAAATCAAAAGAATAG
ACCGAGATAGGGTTGAGTGTTGTTCCAGTTTGGAACAAGAGTCCACTATTAAAGAAC
GTGGACTCCAACGTCAAAGGGCGAAAAACCGTCTATCAGGGCGATGGCCCACTACG
TGAACCATCACCCTAATCAAGTTTTTTGGGGTCGAGGTGCCGTAAAGCACTAAATCG
GAACCCTAAAGGGAGCC CCCGATTTAGAGCTTGACGGGGAAAGCCGGCGAACGTGG
CGAGAAAGGAAGGGAAGAAAGCGAAAGGAGCGGGCGCTAGGGCGCTGGCAAGTGT
AGCGGTCACGCTGCGCGTAACCACCACACCCGCCGCGCTTAATGCGCCGCTACAGG
GCGCGTCCCATTCGCCATTCAGGCTGCGCAACTGTTGGGAAGGGCGATCGGTGCGG
GCCTCTTCGCTATTACGCCAGCTGGCGAAAGGGGGATGTGCTGCAAGGCGATTAAGT
TGGGTAACGCCAGGGTTTTCCCAGTCACGACGTTGTAAAACGACGGCCAGTGAGCG
CGCGTAATACGACTCACTATAGGGCGAATTGGGTACCGGGCCCCCCCTCGAGGTCG
ACGGTATCGATAAGCTTGATATCGAATTCCTGCAGCCCGGGGGATCCACTAGTTCTA
GAGCGGCCGCCACCGCGGTGGAGCTCCAGCTTTTGTTCCCTTTAGTGAGGGTTAATT
GCGCGCTTGGCGTAATCATGGTCATAGCTGTTTCCTGTGTGAAATTGTTATCCGCTCA
CAATTCCACACAACATACGAGCCGGAAGCATAAAGTGTAAAGCCTGGGGTGCCTAA
TGAGTGAGCTAACTCACATTAATTGCGTTGCGCTCACTGCCCGCTTTCCAGTCGGGA
AACCTGTCGTGCCAGCTGCATTAATGAATCGGCCAACGCGCGGGGAGAGGCGGTTT
GCGTATTGGGCGCTCTTCCGCTTCCTCGCTCACTGACTCGCTGCGCTCGGTCGTTCGG
CTGCGGCGAGCGGTATCAGCTCACTCAAAGGCGGTAATACGGTTATCCACAGAATC
AGGGGATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCCTGCCGCTT
ACCGGATACCTGTCCGCCTTTCTCCCTTCGGGAAGCGTGGCGCTTTCTCATAGCTCAC
GCTGTAGGTATCTCAGTTCGGTGTAGGTCGTTCGCTCCAAGCTGGGCTGTGTGCACG
AACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGC
AGAGCGAGGTATGTAGGCGGTGCTACAGAGTTCTTGAAGTGGTGGCCTAACTACGG
CTACACTAGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGGTT
TTTTTGTTTGCAAGCAGCAGATTACGCGCAGAAAAAAAGGATCTCAAGAAGATCCTT
TGATCTTTTCTACGGGGTCTGACGCTCAGTGGAACGAAAACTCACGTTAAGGGATTT
TGGTCATGAGATTATCAAAAAGGATCTTCACCTAGATCCTTTTCGACCGAATAAATA
CCTGTGACGGAAGATCACTTCGCAGAATAAATAAATCCTGGTGTCCCTGTTGATACC
GGGAAGCCCTGGGCCAACTTTTGGCGAAAATGAGACGTTGATCGGCACGTAAGAGG
TTCCAACTTTCACCATAATGAAATAAGATCACTACCGGGCGTATTTTTTGAGTTGTCG
AGATTTTCAGGAGCTAAGGAAGCTAAAATGGAGAAAAAATCACTGGATATACCAC
CGTTGATATATCCCAATGGCATCGTAAAGAACATTTTGAGGCATTTCAGTCAGTTGC
TCAATGTACCTATAACCAGACCGTTCAGCTGGATATTACGGCCTTTTTAAAGACCGT
AAAGAAAAATAAGCACAAGTTTTATCCGGCCTTTATTCACATTCTTGCCCGCCTGAT
GAATGCTCATCCGGAATTACGTATGGCAATGAAAGACGGTGAGCTGGTGATATGGG
ATAGTGTTCACCCTTGTTACACCGTTTTCCATGAGCAAACTGAAACGTTTTCATCGCT
CTGGAGTGAATACCACGACGATTTCCGGCAGTTTCTACACATATATTCGCAAGATGT
GGCGTGTTACGGTGAAAACCTGGCCTATTTCCCTAAAGGGTTTATTGAGAATATGTT

```
TTTCGTCTCAGCCAATCCCTGGGTGAGTTTCACCAGTTTTGATTTAAACGTGGCCAAT
ATGGACAACTTCTTCGCCCCCGTTTTCACCATGGGCAAATATTATACGCAAGGCGAC
AAGGTGCTGATGCCGCTGGCGATTCAGGTTCATCATGCCGTTTGTGATGGCTTCCAT
GTCGGCAGAATGCTTAATGAATTACAACAGTACTGCGATGAGTGGCAGGGCGGGGC
GTAATTTTTTTAAGGCAGTTATTGGTGCCCTTAAACGCCTGGTTGCTACGCCTGAATA
AGTGATAATAAGCGGATGAATGGCAGAAATTCGAAAGCAAATTCGACCCGGTCGTC
GGTTCAGGGCAGGGTCGTTAAATAGCCGCTTATGTCTATTGCTGGTTTACCGGTTTAT
TGACTACCGGAAGCAGTGTGACCGTGTGCTTCTCAAATGCCTGAGGCCAGTTTGCTC
AGGCTCTCCCCGTGGAGGTAATAATTGACGATATGATCCTTTTTTTCTGATCAAAAG
TGCTCATCATTGGAAAACGTTCTTCGGGGCGAAAACTCTCAAGGATCTTACCGCTGT
TGAGATCCAGTTCGATGTAACCCACTCGTGCACCCAACTGATCTTCAGCATCTTTTAC
TTTCACCAGCGTTTCTGGGTGAGCAAAAACAGGAAGGCAAAATGCCGCAAAAAAGG
GAATAAGGGCGACACGGAAATGTTGAATACTCATACTCTTCCTTTTTCAATATTATT
GAAGCATTTATCAAGGGTTATTGTCTCATGAGCGGATACATATTTGAATGTATTTAG
AAAAATAAACAAATAGGGGTTCCGCGCACATTTCCCCGAAAAGTGCCAC
```

FIG. 5B

METHOD FOR TRANSFER OF DNA SEGMENTS

BACKGROUND OF THE INVENTION

The most common manipulation of vectors in molecular biology laboratories is the transfer of a gene of interest into a vector of choice. The resulting recombinant vectors allow specialized applications such as expression in mammalian cells, expression in bacterial hosts, purification of the native protein through employment of specialized (vector provided) purification tags or detection of interaction with other proteins (two-hybrid systems). Typically, cloning is achieved through restriction digestion, isolation of the desired fragments and reconstitution of the desired plasmid by ligation. Although this technique has been routinely employed for approximately 20 years, it is still error-prone and cumbersome.

There is a need in the art for a method of transferring a desired coding region to a vector of interest without the use of restriction enzyme recognition sites and restriction enzymes. In prior art methods, multiple restriction enzymes are employed for the removal of the desired coding region and the reaction conditions used for each enzyme may differ such that it is necessary to perform the excision reactions in separate steps. In addition, it may be necessary to remove a particular enzyme used in an initial restriction enzyme reaction prior to completing all restriction enzyme digestions. This requires a time-consuming purification of the subcloning intermediate. More recently, recombinase-based cloning methods have been developed. However, the current methods require multiple recombination events.

There is a need in the art for cloning of newly discovered sequences, such as new genes. Thus there is a need in the art for more efficient techniques for transfer of the genes of interest into a vector of choice. It is desirable that such a technique permits high fidelity, high efficiency and a minimum number of handling steps to allow adaptation to automated procedures.

There is a need in the art for a method for the cloning of a DNA molecule which permits rapid transfer of the DNA molecules from one vector to another without the need to rely upon restriction enzyme digestions.

SUMMARY OF THE INVENTION

The present invention provides a method of transfer of a gene of interest to a product vector comprising: contacting in vitro (1) a first vector comprising (a) a gene of interest, (b) a gene encoding a first selectable marker, (c) a double-stranded origin of replication of a rolling circle replicon, and (d) a site-specific recombination recognition site, wherein the gene of interest is interposed between the double-stranded origin of replication of a rolling circle replicon and the site-specific recombination recognition site; (2) a second vector comprising (a) a negative selectable marker, (b) a double-stranded origin of replication of a rolling circle replicon, (c) a site-specific recombination recognition site, (d) a single-stranded origin of replication, and (e) a gene encoding a second selectable marker, wherein the gene encoding the negative selectable marker is interposed between the double-stranded origin of replication of a rolling circle replicon and the site-specific recombination recognition site; and (3) a site-specific recombinase, wherein the contacting permits formation of a co-integrate vector comprising the first and the second vector. The co-integrate vector is subsequently introduced into a prokaryotic host cell so as to permit the formation of a product vector comprising the gene of interest interposed between the double-stranded origin of replication of the second vector and the site-specific recombination recognition site, the single-stranded origin of replication of the second vector, and the gene encoding the second selectable marker, wherein the product vector does not include both of the gene encoding the negative selectable marker and the gene encoding the first selectable marker.

The present invention further provides a method of transfer of a gene of interest to a co-integrate vector comprising contacting in vitro (1) a first vector comprising (a) a gene of interest, (b) a gene encoding a first selectable marker, (c) a double-stranded origin of replication of a rolling circle replicon; and (c) a site-specific recombination recognition site, wherein the gene of interest is interposed between the double-stranded origin of replication of a rolling circle replicon and the site-specific recombination recognition site; (2) a second vector comprising (a) a negative selectable marker, (b) a double-stranded origin of replication of a rolling circle replicon, (c) a site-specific recombination recognition site, (d) a single-stranded origin of replication, and (e) a gene encoding a second selectable marker, wherein the gene encoding the negative selectable marker is interposed between the double-stranded origin of replication of a rolling circle replicon and the site-specific recombination recognition site; and (3) a site-specific recombinase, wherein the contacting permits formation of a co-integrate vector comprising the first and the second vector.

In one embodiment, the co-integrate vector is introduced into a prokaryotic host cell.

The present invention further provides a method of transfer of a gene of interest to a product vector comprising introducing into a prokaryotic host cell which expresses a gene encoding a site-specific recombinase (1) a first vector comprising (a) a gene of interest, (b) a gene encoding a first selectable marker, (c) a double-stranded origin of replication of a rolling circle replicon; and (d) a site-specific recombination recognition site, wherein the gene of interest is interposed between the double-stranded origin of replication of a rolling circle replicon and the site-specific recombination recognition site; and (2) a second vector comprising (a) a negative selectable marker, (b) a double-stranded origin of replication of a rolling circle replicon, (c) a site-specific recombination recognition site, (d) a single-stranded origin of replication, and (e) a gene encoding a second selectable marker, wherein the negative selectable marker is interposed between the double-stranded origin of replication of a rolling circle replicon and the site-specific recombination recognition site, and wherein said prokaryotic host cell further expresses a gene encoding a rep protein which can initiate replication at the double stranded origin of replication. The introduction of the first and second vector to the prokaryotic host cell permits formation of a product vector comprising the gene of interest interposed between the double-stranded origin of replication of the second vector and the site-specific recombination recognition site, the single-stranded origin of replication of the second vector, and the gene encoding the second selectable marker, the product vector not including both of the negative selectable marker and the gene encoding the first selectable marker.

The present invention further provides a method of transfer of a gene of interest to a co-integrate vector comprising introducing into a prokaryotic host cell which expresses a gene encoding a site-specific recombinase a first vector and a second vector so as to permit recombination of the first and second vectors to produce a co-integrate vector, wherein the first vector comprises (a) a gene of interest, (b) a gene encoding a first selectable marker, (c) a double-stranded origin of replication of a rolling circle replicon, and (d) a site-specific recombination recognition site, wherein the gene of interest is interposed between the double-stranded origin of replication of a rolling circle replicon and the site-specific recombination recognition site; and the second vector comprises (a) a negative selectable marker, (b) a double-stranded origin of replication of a rolling circle replicon, (c) a site-specific recombination recognition site, (d) a single-stranded origin of replication, and (e) a gene encoding a second selectable marker, wherein the gene encoding the negative selectable marker is interposed between the double-stranded origin of replication of a rolling circle replicon and the site-specific recombination recognition site.

In one embodiment the introduction of the first and second vector to the host cell permits formation of a product vector comprising the gene of interest interposed between the double-stranded origin of replication of the second vector and the site-specific recombination recognition site, the single-stranded origin of replication of the second vector, and the gene encoding the second selectable marker, wherein said host cell expresses a gene encoding a rep protein which can initiate replication at the double stranded origin of replication of the first and second vector. The product vector does not include both of the negative selectable marker and the gene encoding the first selectable marker.

In a preferred embodiment, the prokaryotic host cell is grown under conditions which permit the first and second vectors to recombine to form a co-integrate vector.

In a further embodiment, following introduction of either the first and second vectors, or the co-integrate vector into the prokaryotic host cell, the product vector is isolated from the host cell.

In a still further embodiment, the first and second selectable markers are different.

In one embodiment, the site-specific recombinase recognition site is selected from the group consisting of: loxP, loxP2, loxP3, loxP23, loxP511, loxB, loxC2, loxL, loxR, loxΔ86, loxΔ117, frt, dif, Kw, λ-att, and ΦC31 att sites.

In one embodiment, the double-stranded origin of replication is the double-stranded origin of replication of the filamentous bacteriophage f1.

In a further embodiment, the double-stranded origin of replication is the double-stranded origin of replication of the plasmid pKym.

In one embodiment, the negative selectable marker is one of rpsL and sacB.

In one embodiment, the gene encoding one of the first or second selectable marker, independently, is selected from the group consisting of: kanarnycin resistance gene, the ampicillin resistance gene, the tetracycline resistance gene, the chloramphenicol resistance gene, spectinomycin resistance gene, gentamycin resistance gene, and the streptomycin resistance gene.

The present invention further provides a vector comprising (a) a negative selectable marker, (b) a double-stranded origin of replication, (c) a site-specific recombination recognition site, and (d) a gene encoding a selectable marker, wherein the negative selectable marker is interposed between the double-stranded origin of replication and the site-specific recombination recognition site.

The invention still further provides a pair of vectors comprising a first vector comprising (a) a gene of interest, (b) a gene encoding a first selectable marker, (c) a double-stranded origin of replication of a rolling circle replicon and (d) a site-specific recombination recognition site, wherein the gene of interest is interposed between the double-stranded origin of replication of a rolling circle replicon and the site-specific recombination recognition site; and a second vector comprising (a) a negative selectable marker, (b) a double-stranded origin of replication of a rolling circle replicon, (c) a site-specific recombination recognition site, (d) a single-stranded origin of replication, and (e) a gene encoding a second selectable marker, wherein the negative selectable marker is interposed between the double-stranded origin of replication of a rolling circle replicon and the site-specific recombination recognition site.

The present invention also provides a product vector comprising (a) a gene of interest, (b) a double-stranded origin of replication of a rolling circle replicon, (c) a site-specific recombination recognition site, (d) a single-stranded origin of replication, and (e) a nucleic acid sequence encoding a second selectable marker, wherein the gene of interest is interposed between the double-stranded origin of replication of a rolling circle replicon and the site-specific recombination recognition site, and wherein the vector does not include both of the gene encoding the negative selectable marker and the gene encoding the first selectable marker.

In addition, the present invention provides a kit for the transfer of a gene of interest to a product vector comprising (1) a first vector comprising (a) a gene of interest, (b) a gene encoding a first selectable marker, (c) a double-stranded origin of replication of a rolling circle replicon, and (d) a site-specific recombination recognition site, wherein the gene of interest is interposed between the double-stranded origin of replication of a rolling circle replicon and the site-specific recombination recognition site; and (2) a second vector comprising (a) a negative selectable marker, (b) a double-stranded origin of replication of a rolling circle replicon, (c) a site-specific recombination recognition site, (d) a single-stranded origin of replication, and (e) a gene encoding a second selectable marker, wherein the gene encoding the negative selectable marker is interposed between the double-stranded origin of replication of a rolling circle replicon and the site-specific recombination recognition site; and (3) packaging materials therefore.

The invention still further provides a kit for the transfer of a gene of interest to a product vector comprising (1) a first vector comprising (a) a cloning site for insertion of a gene of interest, (b) a gene encoding a first selectable marker, (c) a double-stranded origin of replication of a rolling circle replicon, and (c) a site-specific recombination recognition site, wherein the cloning site for insertion of a gene of interest is interposed between the double-stranded origin of replication of a rolling circle replicon and the site-specific recombination recognition site; and (2) a second vector comprising (a) a negative selectable marker, (b) a double-stranded origin of replication of a rolling circle replicon, (c) a site-specific recombination recognition site, (d) a single-stranded origin of replication, and (e) a gene encoding a second selectable marker, wherein the negative selectable marker is interposed between the double-stranded origin of replication of a rolling circle replicon and the site-specific recombination recognition site; and (3) packaging materials therefore.

In one embodiment, the kit further comprises a host cell capable of supporting a rolling circle double-stranded origin of replication.

In a further embodiment, the kit further comprises a site-specific recombinase.

In a still further embodiment, the kit comprises a host cell comprising a site-specific recombinase specific for the site-specific recombination site.

In a still further embodiment of the invention, the host cell is transfectible.

As used herein, "interposed" refers to a nucleic acid molecule which has, immediately adjacent to its 5' most end, either a double-stranded origin of replication of a rolling circle replicon or a site-specific recombination recognition site, and has, immediately adjacent to its 3' most end whichever of the double-stranded origin of replication of a rolling circle replicon or site-specific recombination recognition site that is not immediately adjacent to the 5' most end. As used herein, "immediately adjacent" means that there are between 0 and 500 nucleotides between the 5' end of the nucleic acid molecule and the 3' nucleotide of a sequence consisting of either a double-stranded origin of replication of a rolling circle replicon or a site-specific recombination recognition site, and between 0 and 500 nucleotides between the 3' end of the nucleic acid molecule and the 5' nucleotide of a sequence consisting of whichever of the a double-stranded origin of replication of a rolling circle replicon or site-specific recombination recognition site is not adjacent to the 5' end of the nucleic acid molecule.

As used herein, "double-stranded origin of replication of a rolling circle replicon" refers to a nucleic acid sequence which contains the physical and functional elements required in cis for the initiation of the first strand synthesis. A "double-stranded origin of replication of a rolling circle replicon" may be isolated from plasmids of both gram-positive and gram-negative bacteria, bacteriophage or any organism which can support replication by a rolling circle mechanism. Such organisms include, but are not limited to Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides, cyanobacteria, Helobacter pylori, Selnomonas ruminatium, Shigella sonnei, Zymomonas mobilis, Mycoplasma mycoides, or Treponema denticola, Bacillus thuringiensis, Staphlococcus lugdunensis, Leuconostoc oenos, Corynebacterium xerosis, Lactobacillus plantarum, Streptococcus faecalis, Bacillus coagulans, Bacillus ceretus, Bacillus popillae, Synechocystis strain PCC6803, Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Staphylococcus epidermidis, Zymomonas mobilis, Streptomyces phaechromogenes, Streptomyces ghanaenis, Escherichia coli, Halobacterium strain GRB, and Halobaferax sp. strain Aa2.2. Examples of plasmids which possess a "double-stranded origin of replication of a rolling circle replicon" useful in the present invention include, but are not limited to the following: pT181, pC221, pC223, pCW7, pHD2, pLUG10, pOg32, pS194, pT127, pTZ12, pUB112, pE194, pA1, pC1305, pCI411, pFX2, pKMK1, pLS1, pSH71, pWV01, pC194, pAMα1, pA, pPL, pSSU1, p1414, pDC123, pBAA1, pBC1, pBC16, pBP614, pBS2, pC300, pCA2.4, pCB101, pCB2.4, pCC5.2, pFTB14, pGT5, pJDB21, pKYM, pLAB1000, pLot3, pLP1, pOX6, pRF1, pRBH1, pSH1415, pSN1981, pTA1060, pTD1, pTHT15, pUB110, pUH1, pVA380-1, pWC1, pEGB32, p353-2, pSN2, pBI143, pE5, pE12, pIM13, pNE131, pT48, pTCS1, pZMO2, pIJ101, pBL1, pJV1, pSG5, pSN22, pC1305, pG12, pGRB1, pHK2, pHPK255, pTX14-1, pTX14-3, or pVT736-1.

As used herein, a "single-stranded origin of replication" refers to a nucleic acid sequence at which replication of single-stranded DNA is initiated. A "single-stranded origin of replication" is strand and orientation specific and must be present in a single-stranded form to actively initiate replication. A "single-stranded origin of replication" useful in the present invention may include any single-stranded origin of replication known to those of skill in the art, or may be selected from ssos, ssoA, ssoT, ssoW, ssoU types of single-stranded origins of replication, or may be selected from the single-stranded origins of replication present in the following plasmids: pT181, pC221, pC223, pCW7, pHD2, pLUG10, pOg32, pS194, pT127, pTZ12, pUB112, pE194, pA1, pC1305, pCI411, pFX2, pKMK1, pLS1, pSH71, pWV01, pC194, pAMα1, pBAA1, pBC1, pBC16, pBP614, pBS2, pA, pPL, pSSU1, p1414, pDC123, pC300, pCA2.4, pCB101, pCB2.4, pCC5.2, pFTB14, pGT5, pJDB21, pKYM, pLAB1000, pLot3, pLP1, pOX6, pRF1, pRBH1, pSH1451, pSN1981, pTA1060, pTD1, pTHT15, pUB110, pUH1, pVA380-1, pWC1, pEGB32, p353-2, pSN2, pBI143, pE5, pE12, pIM13, pNE131, pT48, pTCS1, pZMO2, pIJ101, pBL1, pJV1, pSG5, pSN22, pC1305, pG12, pGRB1, pHK2, pHPK255, pTX14-1, pTX14-3, PCR-ScriptAmpSK$^+$, filamentous phage (f1), $\Phi$X174, pB#322, or pVT736-1

As used herein, "rolling circle replication" refers to a mode of replication utilized by some DNA molecules including certain bacteriophage genomes and also found in Xenopus oocytes during amplification of extrachromosomal ribosomal DNA. DNA synthesis initiates at a double-stranded origin of replication from which a sole replication fork proceeds around the template nucleic acid. As the fork revolves, the newly synthesized strand displaces the previously synthesized strand from the template, producing a characteristic tail comprised of single-stranded DNA. The displaced strand is released from the plasmid once the replication fork encounters the double-stranded origin of replication, recircularized and may then be made double-stranded via DNA synthesis which initiates from the single-stranded origin of replication and processed into single or multimeric copies of the original DNA.

As used herein, a "site-specific recombinase" refers to an enzyme that binds a specific DNA recognition sequence within a first DNA molecule and, upon forming a protein DNA complex at this specific recognition site, promotes strand exchange with a second protein DNA complex which includes a second molecule of the same "site-specific recombinase" bound to a different site on the first DNA molecule or a second DNA molecule having the same recognition sequence, recombining the first and second DNA sequences adjacent to each recombinase recognition site to form a recombined DNA which includes sequences of both the first and second DNA molecules.

As used herein, a "site-specific recombination recognition site" refers to a nucleic acid sequence (i.e., site) which is recognized by a sequence-specific recombinase and which becomes, or is adjacent to the crossover region during the site-specific recombination event. Examples of site-specific recombination sites include, but are not limited to loxP, loxP2, loxP3, loxP23, loxP511, loxB, loxC2, loxL, loxR, loxΔ86, or loxΔ117 sites, frt sites, $\Phi$C31 att sites, Kw sites, and dif sites.

As used herein, "vector" refers to a nucleic acid molecule that is able to replicate in a host cell. A "vector" is also a "nucleic acid construct". The terms "vector" or "nucleic acid construct" includes circular nucleic acid constructs such as plasmid constructs, cosmid vectors, etc. as well as linear nucleic acid constructs (e.g., PCR products, N15 based linear plasmids form E. coli). The nucleic acid construct may comprise expression signals such as a promoter and/or enhancer (in such a case it is referred to as an expression vector). Alternatively, a "vector" useful in the present invention can refer to an exogenous nucleic acid molecule which is integrated in the host chromosome, providing that the integrated nucleic acid molecule, in whole, or in part, can be converted back to an autonomously replicating form.

As used herein, "selectable marker" refers to any one of numerous markers which permit selection of a cell containing a vector expressing the marker known in the art. For example, a gene coding for a product which confers antibiotic resistance to the cell, which confers prototrophy to an auxotrophic strain, or which complements a defect of the host. A "selectable marker" may be a protein necessary for the survival or growth of a transformed host cell grown in a selective culture medium. Host cells not transformed with the vector containing the selectable marker will not survive in the selective culture medium. Typical selectable markers are proteins that confer resistance to antibiotics or other toxins, such as ampicillin, neomycin, kanamycin, chloramphenicol, streptomycin, spectinomycin, gentamycin, or tetracycline. Alternatively, selectable markers may encode proteins that complement auxotrophic deficiencies or supply critical nutrients not available from complex media, e.g., the gene encoding D-alanine racemase for Bacilli. Alternative selectable markers, useful in the present invention are suppressor tRNAs. A number of selectable markers are known to those of skill in the art and are described for instance in Sambrook et al., Molecular Cloning: A Laboratory Manual (2nd Ed.), Vol. 1–3, Cold Spring Harbor Laboratory, Cold Spring Harbor, N.Y., 1989.

As used herein, a "negative selectable marker" refers to a protein which, when expressed by a host cell confers susceptibility of that host cell to agents such as one of the selectable markers referred to above, e.g., an antibiotic or toxin. Genes encoding "negative selectable markers" useful in the present invention include, but are not limited to rpsL, sacB, hsv-tk, GLUT-2, or gpt. Alternatively, promoters or other functional elements required for the efficient expression of a negative selectable marker gene also can function as negative selectable markers. Alternatively, a negative selectable marker may be a restriction site, recognized by a host restriction system which would lead to cleavage of a plasmid containing the sequence, thus eliminating the functionality of the plasmid. An additional example of a negative selectable marker, useful in the present invention is the so called kill genes derived from low copy number plasmids such as the F' derived ccd gene (Boe et al., 1987 *J. Bacteriol* 169:4646). Insertion of a "negative selectable marker" into a vector of the present invention would permit one of skill in the art to selectively eliminate that vector.

As used herein, "introducing" refers to the transfer of a nucleic acid molecule from outside a host cell to inside a host cell. Nucleic acid molecules may be "introduced" into a host cell by any means known to those of skill in the art, or taught in numerous laboratory texts and manuals such as Sambrook et al. *Molecular Cloning: A Laboratory Manual, 2nd* Ed., Cold Spring Harbor Laboratory Press, New York (1989). Means of "introducing" nucleic acid into a host cell include, but are not limited to heat shock, calcium phosphate transfection, electroporation, lippofection, and viral mediated gene transfer.

As used herein, a "prokaryotic host cell" refers to any organism which can replicate plasmid DNA by a rolling circle mechanism, including, but not limited to gram-positive bacteria, and gram-negative bacteria. Alternatively a "prokaryotic host cell" refers to any organism which is capable of supporting replication from a single-stranded origin of replication. As used herein, a "prokaryotic host cell" also refers to any organism which is capable of supporting nucleic acid replication from both double- and single-stranded origins of replication. More specifically, a "prokaryotic host cell" useful in the present invention may be selected from the group including, but not limited to *Staphylococcus aureus, Escherichia coli, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans*, Bacteroides, cyanobacteria, *Escherichia coli, Helobacter pylori, Selnomonas ruminatium, Shigella sonnei, Zymomonas mobilis, Mycoplasma mycoides*, or *Treponema denticola, Bacillus thuringiensis, Staphlococcus lugdunensis, Leuconostoc oenos, Corynebacterium xerosis, Lactobacillus plantarum, Streptococcus faecalis, Bacillus coagulans, Bacillus ceretus, Bacillus popillae*, Synechocystis strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Staphylococcus epidermidis, Zymomonas mobilis, Streptomyces phaechromogenes, Streptomyces ghanaensis*, Halobacterium strain GRB, and Halobaferax sp. strain Aa2.2.

An advantage of the present invention is that it provides a method for the improved transfer of a gene of interest from one vector to another, without the need for the traditional steps of restriction enzyme digestion, purification, and ligation. A further advantage of the present invention is that it provides a method of transfer of genes of interest into a vector of choice with high fidelity, high efficiency, and a minimal number of handling steps which would allow for the adaptation of the present invention to automated procedures.

Further features and advantages of the invention will become more fully apparent in the following description of the embodiments and drawings thereof, and from the claims

BRIEF DESCRIPTION OF THE FIGURES

FIG. 5 shows the nucleotide sequence of plasmid pBC SK+ (SEQ ID NO: 1) which was used to construct the first and second vectors of FIGS. 3 and 4, respectively.

DETAILED DESCRIPTION

Figure 1:
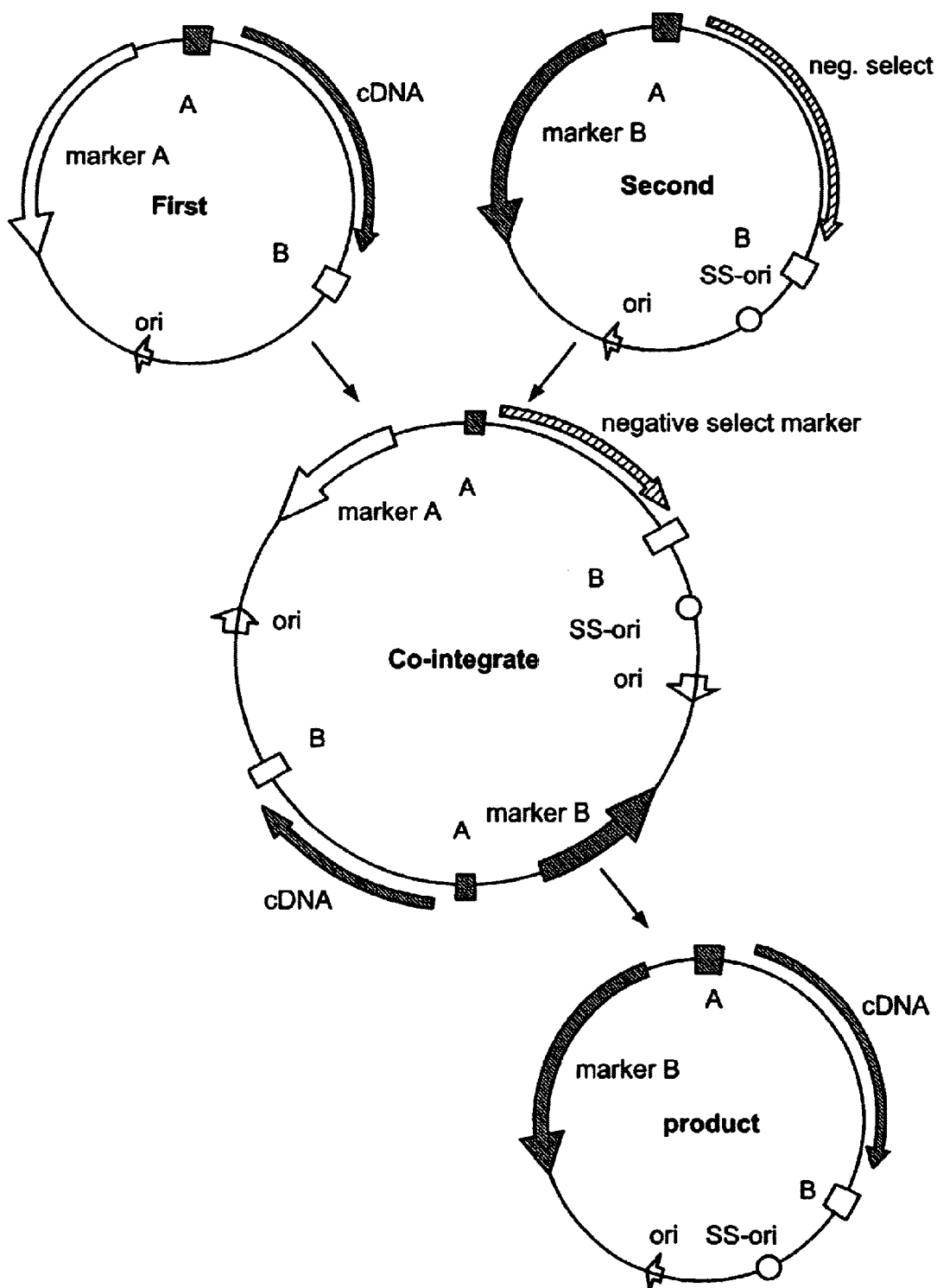
FIG. 1 is a schematic diagram showing the first, second, co-integrate, and product plasmids of the present invention, wherein A represents a site-specific recombinase recognition sequence and B represents a double-stranded origin of replication.

The present invention provides a method of transfer of a gene of interest from a first vector to a product vector comprising contacting a first vector comprising (a) a gene of interest interposed between a double-stranded origin of replication of a rolling circle replicon, and a site-specific recombination recognition site, and (b) a gene encoding a first selectable marker; and a second vector comprising (a)

a negative selectable marker interposed between a double-stranded origin of replication of a rolling circle replicon and a site-specific recombinase recognition site, (b) a single-stranded origin of replication and (c) a gene encoding a second selectable marker in vitro with a site-specific recombinase so as to generate a co-integrate vector. The method subsequently provides for the introduction of the co-integrate vector into a prokaryotic host cell so as to permit the production of the product vector comprising (a) the gene of interest from the first vector interposed between a double-stranded origin of replication and a site-specific recombination recognition site, (b) the single-stranded origin of replication of the second vector, and (c) the gene encoding the selectable marker of the second vector.

Vector Components

The present invention is based, in part, on the construction of two vectors, a first vector and a second vector, and subsequent fusion of the two vectors into a co-integrate vector. The first vector necessarily contains a site-specific recombinase recognition site which dictates where the subsequent recombination event to form the co-integrate vector will occur, a selectable marker gene, a double-stranded origin of replication derived from a plasmid vector which replicates by a rolling circle mechanism, and a gene of interest which is ultimately to be transferred to a product vector. The second vector contains a second selectable marker, a negative selectable marker, a double-stranded origin of replication, and a single-stranded origin of replication. Using a sequence-specific recombinase which acts at the sites dictated by the recombinase recognition sites of the first and second vectors, a precise fusion of the first and second vectors is catalyzed. An advantage of the invention is that transfer of the gene of interest to a product vector occurs without the need to use restriction enzymes.

Double-stranded Origin of Replication of a Rolling Circle Replicon

The formation of a product vector of the present invention depends upon the replication of the co-integrate, by a rolling circle mechanism. Accordingly, both of the first and second vectors which are recombined to generate the co-integrate vector must contain a double-stranded origin of replication. The double-stranded origin of replication of a rolling circle replicon contains the physical and function elements required in cis for the initiation of the leading strand synthesis in the process of rolling circle replication. A double-stranded origin of replication of a rolling circle replicon, useful in the present invention, may be isolated from any plasmid vector, known to those of skill in the art, which replicates by a rolling circle mechanism. Plasmids from which double-stranded origins of replication of a rolling circle replicon may be obtained include, but are not limited to the following: pT181, pC221, pC223, pCW7, pHD2, pLUG10, pOg32, pS194, pT127, pTZ12, pUB112, pE194, pA1, pC1305, pCI411, pFX2, pKMK1, pLS1, pSH71, pWV01, pC194, pAMα1, pBAA1, pBC1, pBC16, pBP614, pBS2, pC300, pCA2.4, pCB101, pCB2.4, pCC5.2, pFTB14, pA, pPL, pSSU1, p1414, pDC123, pGT5, pJDB21, pKYM, pLAB1000, pLot3, pLP1, pOX6, pRF1, pRBH1, pSH1451, pSN1981, pTA1060, pTD1, pTHT15, pUB110, pUH1, pVA380-1, pWC1, pEGB32, p353-2, pSN2, pBI143, pE5, pE12, pIM13, pNE131, pT48, pTCS1, pZMO2, pIJ101, pBL1, pJV1, pSG5, pSN22, pC1305, pG12, pGRB1, pHK2, pHPK255, pTX14-1, pTX14-3, pVT736-1, and $E.$ $coli$ phages such as f1 and ΦX174. The fully functional double-stranded origin of replication generally consists of less than 100 base pairs, and is comprised of two general regions, one which is involved in sequence-specific, non-covalent binding to the protein which initiates replication, and the second which contains the site at which a nick is produced in the plasmid vector DNA for the start of replication. Replication is generally initiated by the introduction of a nick within a sequence which is generally conserved in all rolling circle replication plasmids except in pKMK1, which has an extra C residue.

Although any rolling circle plasmid double-stranded origin of replication may be used for production of the product plasmid, its usefulness is often diminished by the minimal size required for its function. The double-stranded origin of replication of a rolling circle replicon is transferred to the product vector along with the gene of interest as described hereinbelow. The small size of the double stranded origin of replication is advantageous for applications which require the translational fusion of open reading frames contained within the transferred gene of interest to sequences contained within the second vector (such as epitope tags, or purification tags). The minimal sequence of the double-stranded origin required to support replication is often poorly defined. An origin of replication useful in the invention is the double-stranded origin of replication of the bacteriophage ΦX174. The minimal sequence for the double-stranded origin of replication is 30 bases long, consisting of the sequence caacttgatattaataacactatagaccac (SEQ ID NO: 2), which initiates replication of the (+) strand (Brown et al. (1983) $J.$ $Biol.$ $Chem.$ 13:8402). The underlined nucleotides show the minimal sequence required for incision by the replication proteins (Fluit et al. (1984) $Virology$ 154:357). The bold sequence is required for binding of the replication proteins to the double-stranded origin (Van Mansfield et al. (1984) $Adv.$ $Exp.$ $Med.$ $Biol.$ 179:221). This origin contains 3 reading frames lacking stop codons (1 in the orientation shown, 2 on the complementary strand), thus allowing formation of translational fusions. In a preferred embodiment, the double stranded origin of replication is the double stranded origin from bacteriophage f1 which comprises the sequence gagtccacgttctttaatagtggactct-tgttccaaactggaacaa (SEQ ID NO: 3). A key feature of the present invention is that in vitro and in vivo replication of a plasmid containing two double-stranded origins of replication on the same strand lead to the formation of two smaller plasmids corresponding to the sequences located between the two double-stranded origins of replication (Fluit et al. $Virology$ 154:357; Goetz and Hurwitz (1988) $J.$ $Biol.$ $Chem.$ 263:16443).

An alternative double-stranded origin of replication useful in the present invention is the double-stranded origin of the rolling circle plasmid pKYM, originally isolated from $Shigella$ $sonnei$ (Sugiura et al. (1984) $J.$ $Biochem.$ 96:1193). pKYM is a plasmid that replicates by the rolling circle mechanism in $E.$ $coli$ (Yasukawa et al. (1991) $Proc.$ $Natl.$ $Acad.$ $Sci.$ $USA$ 88:10282). When certain mutants of the plasmid encoded replication protein are used, the minimal sequences required for double-stranded origin of replication function is 5'-TTGTATTTATACTTAAGGGATAAATGGC GGATATGAAATAGT-3' (SEQ ID NO: 4).

In addition to the double stranded origins of replication from ΦX174 and pKYM, sequences the double stranded origin of replication from other plasmids which replicate by a rolling circle mechanism may also be used. Additional double stranded origins of replication useful in the present invention include, but are not limited to the double stranded origins of replication from: pA (5'-CAGGTATGCGGA AAACTTTAGGAACAAGG-3'; SEQ ID NO: 5; GenBank Accession No: 10956566), pBL (5'-ACTTATCTTGAT AATAAGGGTAACTATTTACGGCG-3'; SEQ ID NO: 6;

GenBank Accession No: 10956242), pSSU1 (5'-GGGGGC GTACTACGACCCCCC-3'; SEQ ID NO: 7; GenBank Accession No: 10956187), p1414 (5'-GTTTTAAAAAAGC CGGCTGTTTCAGCCGGCTTTTTTTCGATTTTGGCGG GGGTCTTTTCTTATCTTGATACTATATAGAAACACC AAGATTTTTTAAAAGCCTTGCGTGTCAAGGCTT-3'; SEQ ID NO: 8; GenBank Accession No: 10956512), and pDC123 (5'-TTTCTCCGAAAAAATCTAAAATATGGGG GGGCTACTACGACCCCCCCTATGCCAAAATCAAAA AAAAAACG-3'; GenBank Accession No: AF167172).

Single-stranded Origin of Replication

Replication of the co-integrate plasmid of the invention from the double-stranded origin of replication produces a single-stranded nucleic acid (DNA) as described in more detail below. Replication of the single-stranded DNA released upon completion of leading strand synthesis initiates from the plasmid single-stranded origin of replication and is carried out solely by the proteins present in the host cell (Khan (1997) *Microbiol. Mol. Biol. Rev.* 61:442; del-Solar et al. (1998) *Microbiol. Mol. Biol. Rev.* 62:434). Sequence and structural similarities has led to the identification of at least four main types of single-stranded origins of replication, termed ssos, ssoA, ssoT, ssoW, and ssoU. While some single-stranded origins of replication function effectively only in their native host organisms, such as ssoA and ssoW, others, such as ssoU and ssoT can support single-stranded to double-stranded DNA synthesis in a broad range of bacterial hosts. Accordingly, single-stranded origins of replication, useful in the present invention are preferable selected from either ssoU or ssoT. The single-stranded origins of replication are strand and orientation specific and must be present in a single-stranded form in order to be active. All single-stranded origins that have been analyzed to date contain single-stranded DNA promoters that are recognized by the host cell RNA polymerase that synthesizes a short RNA primer for DNA synthesis (Kramer et al. (1997) *EMBO J.* 16:5784; Kramer (1998) *Proc. Natl. Acad. Sci. USA* 95:10505).

In addition to the general categories of single-stranded origins of replication (i.e., ssoU, ssoT), single-stranded origins of replication, useful in the present invention may be selected from any plasmid which replicates by a rolling circle mechanism including, but not limited to the following: pT181, pC221, pC223, pCW7, pHD2, pLUG10, pOg32, pS194, pT127, pTZ12, pUB112, pE194, pA1, pC1305, pCI411, pFX2, pKMK1, pLS1, pSH71, pWV01, pC194, pAMα1, pBAA1, pBC1, pBC16, pBP614, pA, pPL, pSSU1, p1414, pDC123, pBS2, pC300, pCA2.4, pCB101, pCB2.4, pCC5.2, pFTB14, pGT5, pJDB21, pKYM, pLAB1000, pLot3, pLP1, pOX6, pRF1, pRBH1, pSH1451, pSN1981, pTA1060, pTD1, pTHT15, pUB110, pUH1, pVA380-1, pWC1, pEGB32, p353-2, pSN2, pBI143, pE5, pE12, pIM13, pNE131, pT48, pTCS1, pZMO2, pIJ101, pBL1, pJV1, pSG5, pSN22, pC1305, pG12, pGRB1, pHK2, pHPK255, pTX14-1, pTX14-3, PCR-ScriptAmpSK⁺, filamentous phage (f1), ΦX174, or pVT736-1. In addition, a single-stranded origin of replication may be derived from a plasmid isolated from a host organism capable of replicating nucleic acid by a rolling circle mechanism including but not limited to *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans*, Bacteroides, cyanobacteria, *Helobacter pylori, Selnomonas ruminatium, Shigella sonnei, Zymomonas mobilis, Mycoplasma mycoides*, or *Treponema denticola, Bacillus thuringiensis, Staphlococcus lugdunensis, Leuconostoc oenos, Corynebacterium xerosis, Lactobacillus plantarum, Streptococcus faecalis, Bacillus coagulans, Bacillus ceretus, Bacillus popillae*, Synechocystis strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Staphylococcus epidermidis, Zymomonas mobilis, Streptomyces phaechromogenes, Escherichia coli, Streptomyces ghanaenis*, Halobacterium strain GRB, and Halobaferax sp. strain Aa2.2.

Examples of plasmid single stranded origins of replication useful in the present invention, include but are not limited to the single stranded origin of replication of the following plasmids: pA (5'-AACAAGGGTTGTTCGCGGGGACAA AACTAGCCCCAAGCTCGCGTTTCCGCCGTTAGTA CCTTGACGCGGCTTTACCCAGCGCGCCTACGCGCC GAGATTT-3'; SEQ ID NO: 10; GenBank Accession No: 10956566), pPL (5'-GTCAACGATAAGCGGACTTCG GCGTTAGCCGATGGAGCATTAAGGAGTTGAT GGTTTCCAGGCTCTTGGCGACAGCAAAAAGGAA AAACACTTTTTCCCTTCCTCGACAGAGCCACCG GACCTAGAAAGAAAGTTTTTGGCTGCCCCTT TGGGCGGTCTTTTTTTGGCCATGCGGAGCATGG CTCGGCGGAGC CGACGGC-3'; SEQ ID NO: 11; GenBank Accession No: 10956242), pSSU1 (5'-GCGATTTAT GCCGAGAAAACTCTTGCTAGGAAGCTATGCGA AATAGACTAAGTCGACAGGCTGAAAGCTTGCCGA CCGAACACGACAGTCAGATTTCAGCTCCTAGCAA GAGGAAA TTGGAATAA-3'; SEQ ID NO: 12; GenBank Accession No: 10956187), p1414 (5'-TGGGGGTGAGT CAACGGTAACCGGACCGTAGGGAGGATTAAGGA GTTGACCCACCCGAACCCTTTCAGCACTCAAACA AACCCGTTTGTTTGACGCCAACGCCCCCCGAAG ATGCGGGGGGTTGGGGGGATTGAATGCTGGC ATCCAACG-3'; SEQ ID NO: 13; GenBank Accession No: 10956512), pDC123 (5'-TATTTGACAACAAGTAACCAA GTGACTGCCGTCCTTTGTCCGTGTCCGTCCAGCCT TTCGGCTCGGCACGTCCTAGCGTACTCTGTCACTG CTTATTGTCA-3'; SEQ ID NO: 14; GenBank Accession No: AF167172), and f1 (5'-AAAAACCGTCTACAGGGC GATGGCCCACTACGTGAACCATCACCCTAATC AAGTTTTTTGGGGTCGAGGTGCCGTAAAGCAC TAAATCGGAACCCTAAAGGGAGCCCCCGATT TAGAGCT; SEQ ID NO: 15; GenBank Accession No. AF305698).

Selectable Markers

The first and second plasmids of the present invention also comprise a gene encoding a selectable marker which may be any marker known in the art, for instance a gene coding for a product which confers antibiotic resistance to the cell, which confers prototrophy to an auxotrophic strain, or which complements a defect of the host. Selectable markers, useful in the present invention, may be a protein necessary for the survival or growth of transformed host cells grown in a selective culture medium. Host cells not transformed with the vector containing the selectable marker will not survive in the culture medium. Typical selectable markers are proteins that confer resistance to antibiotics or other toxins, such as ampicillin (GenBank Accession No: AF307748), neomycin (GenBank Accession No: U89929), kanamycin (GenBank Accession No: AF292560), chloramphenicol (GenBank Accession No: 11061044), or tetracycline (GenBank Accession No: U49939). Alternatively, selectable markers may encode proteins that complement auxotrophic deficiencies or supply critical nutrients not available from complex media, e.g., the gene encoding D-alanine racemase for Bacilli. Alternatively, a selectable marker, useful in the present invention, can be a suppressor tRNA. A number of selectable markers are known to those of skill in the art and are described for instance in Sambrook et al., Molecular Cloning: A Laboratory Manual (2nd Ed.), Vol. 1–3, Cold Spring Harbor Laboratory, Cold Spring Harbor, N.Y., 1989. According to the methods of the present invention, it is preferred that the selectable marker of the first vector is different from the selectable marker of the second plasmid, thus allowing for the independent selection of either the first or second plasmid.

Negative Selectable Marker

One or more plasmids of the present invention further comprises a negative selectable marker which provides a mechanism by which plasmids that express the negative selectable marker may be selected against. Negative selectable markers useful in the present invention are proteins which, when expressed by a host cell confers susceptibility of that host cell to agents such as antibiotics or toxins. Genes encoding negative selectable markers useful in the present invention include, but are not limited to rpsL (GenBank Accession No: AF316617), hsv-tk (U.S. Pat. No: 6,146,888, incorporated herein by reference), gpt (U.S. Pat. No: 6,063,630, incorporated herein by reference), GLUT-2 (U.S. Pat. No: 6,110,707, incorporated herein by reference), and sacB (GenBank Accession No: U75992). Alternatively, promoters or other functional elements required for the efficient expression of a negative selectable marker gene also can function as negative selectable markers. Alternatively, a negative selectable marker may be a restriction site, recognized by a host restriction system which would leas to cleavage of a plasmid containing the sequence, thus eliminating the functionality of the plasmid. An additional example of a negative selectable marker, useful in the present invention is the so called kill genes derived from low copy number plasmids such as the F' derived ccd gene (Boe et al., 1987 *J. Bacteriol* 169:4646). In preferred embodiments of the present invention the negative selectable marker is the protein encoded by the *E. coli* rpsL gene. Expression of the wild type rpsL gene confers streptomycin sensitivity to a streptomycin host strain and thus cells which express rpsL may be selected against by treating the cells with streptomycin.

Site-specific Recombination Recognition Sites

The plasmids of the present invention comprise either a gene of interest or a negative selectable marker interposed between a double-stranded origin or replication and a site-specific recombination recognition site. The precise fusion between the first and second vector is catalyzed by a site-specific recombinase. Site-specific recombinases are enzymes that recognize a specific DNA site or sequence termed a site-specific recombination recognition site, and catalyzes the recombination of DNA in relation to these sites. Conversely, site-specific recombination recognition sequences are short nucleic acid sequence or site which is recognized by a sequence-or site-specific recombinase and which become the crossover regions during the site-specific recombination event. Examples of site-specific recombination sites include, but are not limited to loxP sites (SEQ ID NO: 16), loxP2 sites, loxP3 sites, loxP23 sites, loxP511 sites (SEQ ID NO: 17), loxB sites (GenBank Accession No: M10512), loxC2 sites (SEQ ID NO: 18), loxL sites (GenBank Accession No: M10511), loxR sites (GenBank Accession No: M10510), loxΔ86 sites, loxΔ117 sites, frt sites (GenBank Accession No: 1769877), λ-phage att sites (GenBank Accession No: NC001416), and dif sites (GenBank Accession No: S62735). Site-specific recombination recognition sites, and site-specific recombination are described in further detail below. In preferred embodiments, the site-specific recombinase recognition sites are loxP sites, or the attP and attB sites recognized by the integrase from ΦC31 (GenBank Accession No. AJ006598; Groth, 2000 *Proc. Natl. Acad. Sci. USA,* 97:5995).

First and Second Vector Recombination

The present invention the transfer of a gene of interest from a first vector to a product vector is achieved by first forming a co-integrate vector through the recombination of the first and second vector at the site-specific recombination recognition site (FIG. 1, Site A), preferably by site-specific recombination. Subsequently, selective rescue of the sequences between the double-stranded origins of replication (FIG. 1, Site B) containing the original second vector sequences and the gene of interest is achieved using the double-stranded origin of replication in a rolling circle host cell.

As described above, and shown in FIG. 1, formation of the co-integrate vector comprised of the source and the acceptor can be achieved by a variety of methods including ligation of restriction digested fragments, ligation independent cloning and recombination. Due to the efficiency, speed, and the low number of handling steps required, the preferred method of co-integrate vector formation is by recombination. Ideally, formation of the co-integrate vector would occur in vivo (i.e., within a bacterial host strain), since this would allow the minimal number of handling steps. This could be achieved either by homologous recombination, or site-specific recombination. However, relatively large regions of homology are required for efficient homologous recombination (Zhang et al. (1998) *Nature Genetics* 20:123). Most site-specific recombination systems require only relatively short specific sequences of typically 30–40 bases (Craig (1988) *Ann. Rev. Gen.* 22:77). However, in vivo site-specific recombinases act mainly as resolvases (i.e., they excise rather than insert), due to the reversibility of most site-specific recombination reactions (Adams et al. (1992) *J. Mol. Biol.* 226:661). Thus, the preferred method of co-integrate vector formation is by in vitro site-specific recombination. This may be achieved using systems such as Cre/loxP (Abremski et al. (1983) *Cell* 32:1301), Flp/Frt (Broach et al. (1982) *Cell* 29:227), or λ-int/attP (Landy (1989) *Ann. Rev. Biochem.* 58:913).

Sequence Specific Recombinases and Recognition Sites

The precise fusion between the first vector and the second vector is preferably catalyzed by a site-specific recombinase. Site-specific recombinases are enzymes that recognize a specific DNA site or sequence (referred to herein generically as a "site-specific recombinase recognition site") and catalyzes the recombination of DNA in relation to these sites. Site-specific recombinases are employed for the recombination of DNA in both prokaryotes and eukaryotes. Examples of site-specific recombination include 1) chromosomal rearrangements which occur in *Salmonella typhimurium* during phase variation, inversion of the FLP sequence during the replication of the yeast 2 μm circle and in the rearrangement of immunoglobulin and T cell receptor genes in vertebrates, and 2) integration of bacteriophages into the chromosome of prokaryotic host cells to form a lysogen.

The present invention is illustrated but not limited by the use of vectors containing loxP sites and the recombination of these vectors using the Cre recombinase of bacteriophage Pl. The Cre protein catalyzes recombination of DNA between two loxP sites (Sternberg et al. (1981) *Cold Spring Harbor Symp. Quant. Biol.* 45:297). The loxP sites may be present on the same DNA molecule or they may be present on different DNA molecules; the DNA molecules may be linear or circular or a combination of both. The loxP site consists of a double-stranded 34 bp sequence (SEQ ID NO: 16) which comprises two 13 bp inverted repeat sequences separated by an 8 bp spacer region (Hoess et al. (1982) *Proc. Natl. Acad. Sci. USA* 79:3398 and U.S. Pat. No. 4,959,317, the disclosure of which is herein incorporated by reference). The internal spacer sequence of the loxP site is asymmetrical and thus, two loxP sites can exhibit directionality relative to one another (Hoess et al. (1984) *Proc. Natl. Acad Sci. USA* 81:1026). When two loxP sites on the same DNA molecule are in a directly repeated orientation, Cre excises the DNA between these two sites leaving a single loxP site on the DNA molecule (Abremski et al. (1983) *Cell* 32:1301). If two loxP sites are in opposite orientation on a single DNA molecule, Cre inverts the DNA sequence between these two sites rather than removing the sequence. Two circular DNA molecules each containing a single loxP site will recombine with another to form a mixture of monomer, dimer, trimer, etc. circles. The concentration of the DNA circles in the reaction can be used to favor the formation of monomer (lower concentration) or multimeric circles (higher concentration).

Circular DNA molecules having a single loxP site will recombine with a linear molecule having a single loxP site to produce a larger linear molecule. Cre interacts with a linear molecule containing two directly repeating loxP sites to produce a circle containing the sequences between the loxP sites and a single loxP site and a linear molecule containing a single loxP site at the site of the deletion.

The Cre protein has been purified to homogeneity (Abremski et al. (1984) *J. Mol. Biol.* 259:1509) and the cre gene has been cloned and expressed in a variety of host cells (Abremski et al. (1983), supra). Purified Cre protein is available from a number of suppliers (e.g., Stratagene, Novagen and New England Nuclear/Du Pont).

The Cre protein also recognizes a number of variant or mutant lox sites (variant relative to the loxP sequence), including the loxB, loxL, loxR, loxΔ86, and loxΔ117 sites which are found in the *E. coli* chromosome (Hoess et al. (1982), supra). Other variant lox sites include loxP511 (5'-ATAACTTCGTATA<u>GTATACAT</u>TATACGAAGTTAT-3' (SEQ ID NO: 17); spacer region underlined; Hoess et al. (1986), supra), loxC2 (5'-ACAACTTCGTATA<u>ATGTATGCT</u>ATACGAAGTTAT-3' (SEQ ID NO: 18); spacer region underlined; U.S. Pat. No. 4,959,317). Cre catalyzes the cleavage of the lox site within the spacer region and creates a six base-pair staggered cut (Hoess and Abremski (1985) *J. Mol. Biol.* 181:351). The two 13 bp inverted repeat domains of the lox site represent binding sites for the Cre protein. If two lox sites differ in their spacer regions in such a manner that the overhanging ends of the cleaved DNA cannot reanneal with one another, Cre cannot efficiently catalyze a recombination event using the two different lox sites. For example, it has been reported that Cre cannot recombine (at least not efficiently) a loxP site and a loxP511 site; these two lox sites differ in the spacer region. Two lox sites which differ due to variations in the binding sites (ie., the 13 bp inverted repeats) may be recombined by Cre provided that Cre can bind to each of the variant binding sites; the efficiency of the reaction between two different lox sites (varying in the binding sites) may be less efficient that between two lox sites having the same sequence (the efficiency will depend on the degree and the location of the variations in the binding sites). For example, the loxC2 site can be efficiently recombined with the loxp site; these two lox sites differ by a single nucleotide in the left binding site.

A variety of other site-specific recombinases may be employed in the methods of the present invention in place of the Cre recombinase. Alternative site-specific recombinases include:

1) the FLP recombinase of the 2pi plasmid of *Saccharomyces cerevisiae* (Cox (1983) *Proc. Natl. Acad Sci. USA* 80:4223) which recognize the frt site which, like the loxP site, comprises two 13 bp inverted repeats separated by an 8 bp spacer (5'-GAAGTTCCTATTC<u>TCTAGAAA</u>GTATAGGAACTTC-3'(SEQ ID NO:19); spacer underlined). The FLP gene has been cloned and expressed in *E. coli* (Cox, supra) and in mammalian cells (PCT International Patent Application PCT/US92/01899, Publication No.: WO 92/15694, the disclosure of which is herein incorporated by reference) and has been purified (Meyer-Lean et al. (1987) *Nucleic Acids Res.* 15:6469; Babineau et al (1985) *J. Biol. Chem.* 260:12313; Gronostajski and Sadowski (1985) *J. Biol. Chem.* 260:12328);

2) the integrase of Streptomyces phage ΦC31 that carries out efficient recombination between the attP site of the phage genome and the attB site of the host chromosome (Groth et al., 2000 *Proc. Natl. Acad Sci. USA*, 97: 5995);

3) the Int recombinase of bacteriophage lambda (lambda-int/attP) (with or without Xis) which recognizes att sites (Weisberg et al. In: Lambda II, supra, pp. 211–250);

4) the xerC and xerD recombinases of *E. coli* which together form a recombinase that recognizes the 28 bp dif site (Leslie and Sherratt (1995) *EMBO J.* 14:1561);

5) the Int protein from the conjugative transposon Tn916 (Lu and Churchward (1994) *EMBO J.* 13:1541);

6) TpnI and the β-lactamase transposons (Levesque (1990) *J. Bacteriol.* 172:3745);

7) the Tn3 resolvase (Flanagan et al. (1989) *J. Mol. Biol.* 206:295 and Stark et al. (1989) *Cell* 58:779);

8) the SpoIVC recombinase of *Bacillus subtilis* (Sato et al. *J. Bacteriol* 172:1092);

9) the Hin recombinase (Galsgow et al. (1989) *J. Biol. Chem.* 264:10072);

10) the Cin recombinase (Hafter et al. (1988) *EMBO J.* 7:3991);

11) the immunoglobulin recombinases (Malynn et al. *Cell* (1988) 54:453); and 12) the FIMB and FIME recombinases (Blomfield et al., 1997 *Mol. Microbiol.* 23:705)

In Vitro Recombination

In preferred embodiments of the present invention, the fusion of a first vector and a second vector is accomplished in vitro using a purified preparation of a site-specific recombinase (e.g., Cre recombinase). The first vector and the second vector are placed in reaction vessel (e.g., a microcentrifuge tube) in a buffer compatible with the site-specific recombinase to be used. For example, when a Cre recombinase (native or a fusion protein form) is employed the reaction buffer may comprise 50 mM Tris-HCl (pH 7.5), 10 mM MgCl$_2$, 30 mM NaCl and 1 mg/ml BSA. When a FLP recombinase is employed, the reaction buffer may comprise 50 mM Tris-HCl (pH 7.4), 10 mM MgCl$_2$, 100 μg/ml BSA (Gronostajski and Sadowski (1985) 260:12320). The concentration of the first vector and the second vector may vary between 100 ng to 1.0 μg of each vector per 20 μl reaction volume with about 0.1 μg of each nucleic acid construct (0.2 μg total) per 20 μl reaction being preferred. The concentration of the site-specific recombinase may be titered under a standard set of reaction conditions to find the optimal concentration of enzyme to be used.

Host cells, useful in the present invention, are subsequently transformed or transfected with the recombination reaction product containing the co-integrate vector, and can include any host cell which is capable of supporting replication of a rolling circle origin of replication, such as gram-positive bacteria. Other organisms which may be transformed or transfected with the vectors of the present invention include, but are not limited to the following: *Staphylococcus aureus, Bacillus subtilis, Clostridium butyricum, Brevibacterium lactofermentum, Streptococcus agalactiae, Lactococcus lactis, Leuconostoc lactis,* Streptomyces, *Actinobacillus actinobycetemcomitans,* Bacteroides, cyanobacteria, *Escherichia coli, Helobacter pylori, Selnomonas ruminatium, Shigella sonnei, Zymomonas mobilis, Mycoplasma mycoides,* or *Treponema denticola, Bacillus thuringiensis, Staphlococcus lugdunensis, Leuconostoc oenos, Corynebacterium xerosis, Lactobacillus plantarum, Streptococcus faecalis, Bacillus coagulans, Bacillus ceretus, Bacillus popillae,* Synechocystis strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Staphylococcus epidermidis, Zymomonas mobilis, Streptomyces phaechromogenes, Streptomyces ghanaenis,* Halobacterium strain GRB, and Halobaferax sp. strain Aa2.2.

In one embodiment, the host cell further comprises a gene encoding a rep protein which is capable of initiating replication at the double-stranded origin of replication of the co-integrate vector. In a preferred embodiment, the rep protein is provided in trans by subsequent infection of the host cell with a recombinant bacteriophage.

In one embodiment, as described below, following first strand synthesis in the host cell described above, the single stranded product plasmid is packaged into a viral vector and introduced into a secondary host. In this instance, the primary host cell described above does not have to be able to support replication from the single-stranded origin of replication, as this function is performed by the secondary host.

Recombination in Prokaryotic Host Cells

In an alternative embodiment, the fusion of a first vector and a second vector may be accomplished in vivo using a host cell that expresses the appropriate site-specific recombinase (e.g., ΦC31-att).

The first vector and the second vector are cotransformed into the host cell using a variety of methods known to the art. A variety of ways have been developed to introduce vectors into cells in culture, and into cells and tissues of an animal or a human patient. Methods for introducing vectors into cells include, for example, heat shock, wherein competent cells are mixed with nucleic acid, incubated on ice for approximately 20 minutes, then placed at 42° C. for 45 seconds, and calcium phosphate-mediated uptake of nucleic acids by a host cell. These techniques are well known to those of skill in the art, and are described in many readily available publications and have been extensively reviewed. Some of the techniques are reviewed in *Transcription and Translation, A Practical Approach,* Hames, B. D. and Higgins, S. J., eds., IRL Press, Oxford (1984), herein incorporated by reference in its entirety, and *Molecular Cloning,* Second Edition, Maniatis et al, Cold Spring Harbor Laboratory Press, Cold Spring Harbor, N.Y. (1989), herein incorporated by reference in its entirety. Alternatively, plasmids may be introduced into host cells by infection with, for example, adenovirus, or by the mating of host cells provided the plasmid to be transferred comprises an origin of transfer (Guiney (1988) *Plasmid* 20:259; Frost et al. (1994) *Microbiol. Rev.* 58:162).

Host cells, useful in the present invention, which may be transformed with the first and second vectors, include any host cell which is capable of supporting the rolling circle origin of replication used in the first and second vectors, such as gram-positive bacteria. Other organisms which may be transformed or transfected with the vectors of the present invention include, but are not limited to the following: *Staphylococcus aureus, Bacillus subtilis, Clostridium butyricum, Brevibacterium lactofermentum, Streptococcus agalactiae, Lactococcus lactis, Leuconostoc lactis,* Streptomyces, *Actinobacillus actinobycetemcomitans,* Bacteroides, cyanobacteria, *Escherichia coli, Helobacter pylori, Selnomonas ruminatium, Shigella sonnei, Zymomonas mobilis, Mycoplasma mycoides,* or *Treponema denticola, Bacillus thuringiensis, Staphlococcus lugdunensis, Leuconostoc oenos, Corynebacterium xerosis, Lactobacillus plantarum, Streptococcus faecalis, Bacillus coagulans, Bacillus ceretus, Bacillus popillae,* Synechocystis strain PCC6803, *Bacillus liquefaciens, Pyrococcus abyssi, Selenomonas nominantium, Lactobacillus hilgardii, Streptococcus ferus, Lactobacillus pentosus, Bacteroides ragilis, Staphylococcus epidermidis, Staphylococcus epidermidis, Zymomonas mobilis, Streptomyces phaechromogenes, Streptomyces ghanaenis,* Halobacterium strain GRB, and Halobaferax sp. strain Aa2.2.

In one embodiment, the host cell further comprises a gene encoding a rep protein which is capable of initiating replication at the double-stranded origin of replication of the co-integrate vector. In a preferred embodiment, the rep protein is provided in trans by subsequent infection of the host cell with a bacteriophage.

In one embodiment, as described below, following first strand synthesis in the host cell described above, the single stranded product plasmid is packaged into a viral vector and introduced into a secondary host. In this instance, the primary host cell described above does not have to be able to support replication from the single-stranded origin of replication, as this function is performed by the secondary host.

Rescue of the Product Plasmid

The present invention provides a method of transfer of a gene of interest from a first vector to a product vector comprising generating a fused vector (the co-integrate vector, described hereinabove) comprising the first vector and a second vector, followed by rescue of the product vector from the fused vector by rolling circle replication.

Figure 2:
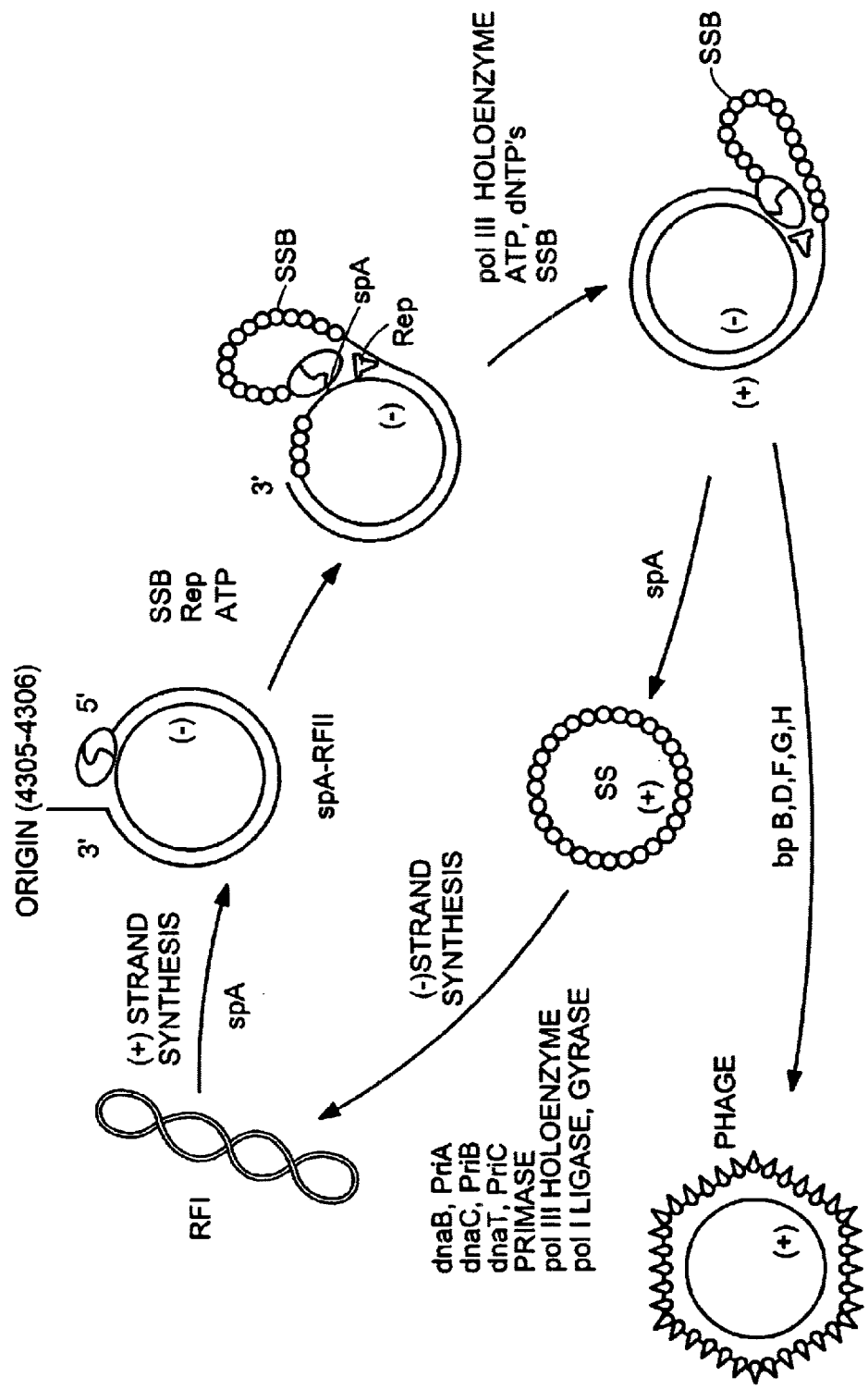
FIG. 2 is a schematic diagram, adapted from Kronberg and Baker, *DNA Replication, 2nd* Ed. 1992, and shows the process of rolling circle replication of plasmid ΦX174.

Replication by the rolling circle mechanism is utilized in a variety of plasmids from gram positive bacteria, some plasmids from gram-negative bacteria and single-stranded bacteriophages (Kornberg and Baker (1992) *DNA Replication* $2^{nd}$ Ed., Freeman and Company, NY; del Solar et al. (1993) *Mol. Microbiol.* 8:789; Khan (1997) *Microbiol. Mol. Biol. Rev.* 61:442). Replication of these replicons involves three steps (FIG. 2). First, an incision is made by a vector encoded protein termed Rep, at the double-stranded origin of replication or (+) origin of replication. The incising protein typically becomes attached to the incised strand 3' to the excision site, often by covalent attachment to the 5' phosphate at the nick site through a tyrosine residue present in the Rep active site. Nicking of the double-stranded origin of replication is followed by recruitment of a DNA helicase and other proteins, such as the single-stranded DNA binding protein and DNA polymerase III. Second, the 5' end of the incision site serves as the priming site for DNA synthesis, progressively replacing the strand with the covalently attached incising protein. When the replication fork reaches the double-stranded origin again, an incision is made in the displaced strand followed by circularization of the ends by ligation. The result is a relaxed, closed circular double-stranded DNA molecule containing the newly synthesized leading strand, and a single-stranded circular molecule consisting of the displaced strand. The nick is then sealed by the host cell DNA ligase, and the double-stranded DNA is then supercoiled by DNA gyrase. In a third step, DNA synthesis is initiated at a site on the single-stranded molecule referred to as the single-stranded origin of replication, or (−) origin of replication, thus converting the single-stranded plasmid into a double-stranded form utilizing only host cell replication factors, proteins, enzymes, etc. It is known that RNA polymerase generally synthesizes an RNA primer from the single-stranded origin, and DNA polymerase I extends this primer, followed by replication by DNA polymerase III. Finally, the DNA ends are joined by DNA ligase, and the resultant double-stranded DNA is supercoiled by DNA gyrase. As a consequence, any sequence located between two double-stranded origins of replication can be converted into a circular plasmid in a host strain providing the incising protein described above, providing a single-stranded origin or replication is present on the (+) strand (Kornberg and Baker (1992) *DNA Replication* $2^{nd}$ Ed., Freeman and Company, NY; del Solar et al. (1993) *Mol. Microbiol.* 8:789; Khan (1997) *Microbiol. Mol. Biol. Rev.* 61:442).

Host cells, useful in the present invention, which may be transformed or transfected with the fused, co-integrate vector, or in alternative embodiments, with the first and second vector are cells which can support rolling circle replication, include gram-positive bacteria, some gram-negative bacteria. Examples of host cells useful in the present invention include, but are not limited to the following: *Staphylococcus aureus, Bacillus subtilis, Clostridium butyricum, Brevibacterium lactofermentum, Streptococcus agalactiae, Lactococcus lactis, Leuconostoc lactis,* Streptomyces, *Actinobacillus actinobycetemcomitans,* Bacteroides, cyanobacteria, *Helobacter pylori, Selnomonas ruminatium, Shigella sonnei, Zymomonas mobilis, Mycoplasma mycoides,* or *Treponema denticola, Bacillus thuringiensis, Staphlococcus lugdunensis, Leuconostoc oenos, Corynebacterium xerosis, Lactobacillus plantarum, Streptococcus faecalis, Bacillus coagulans, Bacillus ceretus, Bacillus popillae,* Synechocystis strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Staphylococcus epidermidis, Zymomonas mobilis, Streptomyces phaechromogenes, Streptomyces ghanaenis,* Halobacterium strain GRB, and Halobaferax sp. strain Aa2.2.

Selection of the Product Vector

The procedure outlined above and in FIG. 1 would involve the use and formation of four plasmid vectors: the first and second vector, the co-integrate vector, and the product vector. Following introduction of the co-integrate vector into a host cell which supports rolling circle replication of the co-integrate vector, or, alternatively, introduction of the first and second vectors into a host cell which supports rolling circle replication, it is advantageous to either selectively eliminate the first, second, and co-integrate vectors, or selectively isolate the product vector.

In preferred embodiments the site-specific recombination reaction occurs in vitro and thus, subsequent transformation of host cells useful in the present invention with the recombination reaction mixture will result in cells which take up the first vector, cells which take up the second vector, and cells which take up the co-integrate vector. One consequence of using a double-stranded origin of replication as a method of retrieving the product vector from the co-integrate vector is that the co-integrate vector remains intact and is maintained in the same host cell with the product vector. This may potentially cause problems in isolation of the product vector due to interference between the two plasmids. It is therefore preferable to prevent this competition. This may be accomplished by either transferring the vectors from original, rolling circle replication host to a new (secondary) host (thereby segregating the product vector from the co-integrate vector) or by generating a co-integrate vector that is replication-incompetent in the host cell.

Plasmid Transfer

Transfer of vectors can be achieved by a variety of methods but is most effectively achieved by mating using an origin of transfer to be included on the second vector. If the host cell contains all genes required for conjugal mating of plasmids, DNA molecules containing this sequence will be efficiently transferred to a new host strain (Guiney (1988) *Plasmid* 20:259; Frost et al. (1994) *Microbiol. Rev.* 58:162). The oriT element, which typically is 100–200 bases in length, can be located anywhere in the transferred plasmid and contains the site where nicking of the plasmid occurs and where transfer of single-stranded DNA is initiated. One potential oriT element which may be utilized in the present invention to initiate transfer of the product vector to a secondary host is that encoded by the nucleotide sequence 5'-AGGCTCTAACAGGTTGGTGGTTCTACCACCAA AAGCACCACACCCCACGCAAAAACAAGTTTTTGC TGATTTTCTTTATAAATAGAGTGTTATGAAAAATTA GTTTCTCTTACTCTCTTTATGATATTTAAAAAAGCG GTGTCGGCGCGGCTACAACAACGCGCCGACACCG TTTTGTAGGGGTGGTACTGACTATTTTTATAAAAAA CATTATTTTATATTAGGGGTGCTGCTAGCGGCGCGG TGTGTTTTTTTATAGGATACCGCTAGGGGCGCTGC TAGCGGTGCG-3' (SEQ ID NO: 20; GenBank Accession No: 9507713), and is the oriT element from the F plasmid (Frost et al. (1994) *Microbiol. Rev.* 58:162). Transfer events may be selected for by co-selection for the marker contained on the transferred plasmid and a marker specific for the new (secondary) host strain.

An alternative method for transfer employs packaging of single-stranded plasmid molecules into phage particles of filamentous phages (Ff phages) such as M13 or F1. Single-stranded DNA molecules will be packaged by Ff phages if a specific, well-defined recognition sequence is present on the single-stranded plasmid (GenBank Accession No: K00967; Dotto and Zinder (1983) *Viology* 154:357; Lopez and Webster (1983) *Virology* 127:177). Thus, infection of the co-integrate vector containing host cells with a non-lytic variant of a filamentous phage such as the M13 derived 704 helper phage (Stratagene, LaJolla, Calif.) will result in formation of infectious particles containing the single-stranded, rescued product vector. Infection of a secondary host will result in effective transfer of the product vector. One advantage of this approach is that only the product vector and not the co-integrate vector will be transferred.

Viral infection of host cell is a technique which is well established in the art and may be found in a number of laboratory texts and manuals such as Sambrook et al., Molecular Cloning: A Laboratory Manual (2nd Ed.), Vol. 1–3, Cold Spring Harbor Laboratory, Cold Spring Harbor, N.Y., 1989. Briefly, in preferred embodiments wherein the host cell is transformed with the in vitro recombination reaction mixture described above, following transformation, the host cells are mixed with a transfer virus, such as the helper phage Exassist (Stratagene, LaJolla, Calif.) and a fresh stationary culture of secondary host cells such as XLOLR-S$^R$ for several hours at 37° C. The helper phage will infect the primary host cell and, due to the packaging signal present in the on the product vector, package the product vector into viral particles. The product-containing viral particles may then infect the secondary host cells, thus transferring the product vector to the secondary host cells. The secondary host cell may then be selected for with, for example, streptomycin, which will selectively eliminate the primary host and the secondary host containing the second vector which contains the wt-rpsL gene that confers streptomycin sensitivity to the otherwise streptomycin resistant secondary host.

Generation of Replication Incompetent Vectors

As an alternative to transfer of the product plasmid into a secondary host, co-integrate vectors may be generated which are replication incompetent in the host cell used for rescue of the product plasmid. Such replication-incompetent co-integrate plasmids may be generated by using N15-based linear plasmids (Rybchin and Svarchevsky (1999) *Mol. Microbiol.* 33:895). These plasmids are based on the lysogenic form of the N15 bacteriophage. They require a plasmid-encoded replication protein and a telomere generating gene product (tel) for replication. If one or both genes are deleted from the plasmid, replication can only occur in strains providing both products in trans. Accordingly, vectors useful in the present invention may be constructed on an N15 backbone, and rendered replication incompetent by introducing them into, for example, tel deficient host cells. Although, the N15-based vector will retain its ability to replicate given the appropriate conditions.

Isolation of the Product Vector

Following selection of host cells comprising the rescued product vector using any of the methods described hereinabove, the product vector may be isolated from either the primary or secondary host cell by any means known in the art, or described in numerous laboratory texts and manuals including Sambrook et al., *Molecular Cloning: A Laboratory Manual* (2nd Ed.), Vol. 1–3, Cold Spring Harbor Laboratory, Cold Spring Harbor, N.Y., 1989. Briefly, the host cell containing the product vector is grown overnight in appropriate medium such as Luria Broth with antibiotics appropriate for the selectable marker expressed by the product vector at 37° C. The host cells are then centrifuged to separate them from the growth medium, and lysed under alkaline conditions. Plasmid DNA may subsequently be purified by cesium chloride high speed centrifugation, followed by ethanol precipitation, or may be purified using commercially available kits such as StrataPrep® (Stratagene, La Jolla, Calif.). Conformation of the identity of the product vector may be performed by any technique known in the art including restriction endonuclease digestion, or Southern analysis.

EXAMPLE 1

Transfer of inserts of interest from a first vector to a product vector is a two step process. The first step is the formation of a fused, co-integrate vector between the first vector and a second vector. The second step is the in vivo rescue of the product vector containing the insert of interest in the second vector using the Double strand origin of replication of a rolling circle replicon. Due to potential problems arising for the co-existence of the co-integrate vector and the rescued product vector in the same host cell, an additional step of transferring the product into a secondary host prior to selection is required.

First Vector Construction

Figure 3:
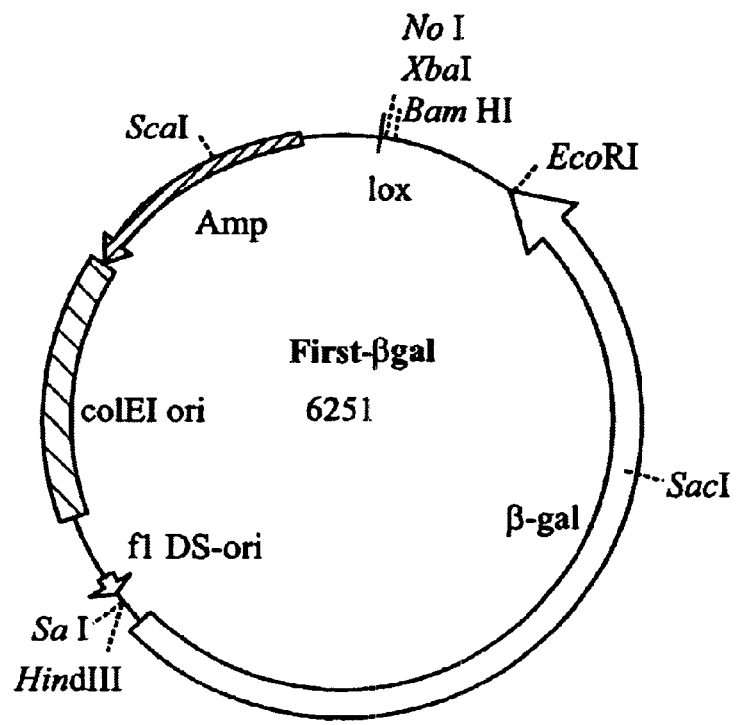
FIG. 3 is a schematic diagram showing the minimum components of the first vector of the present invention.
Figure 4:
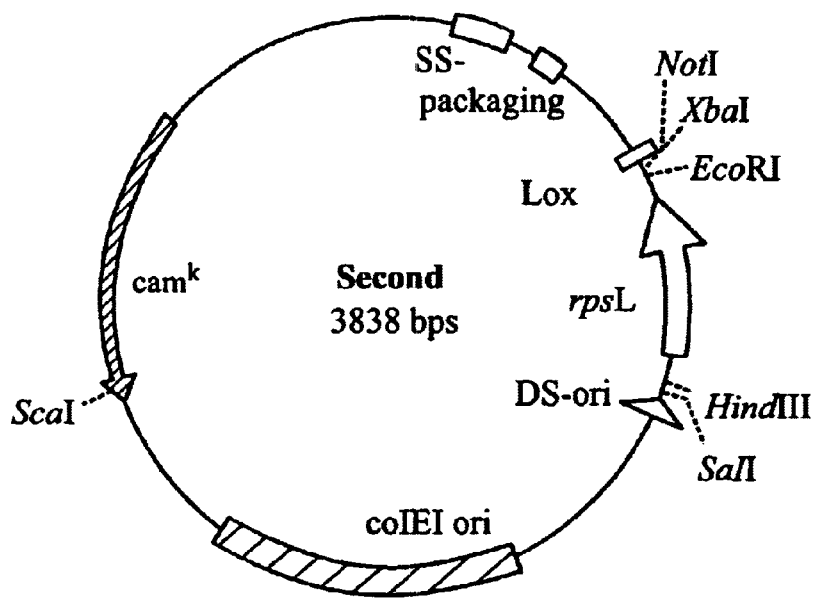
FIG. 4 is a schematic diagram showing the minimum components of the second vector of the present invention.

In order to test the feasibility of insert transfer by the above method, a first vector containing a LoxP site and a 46 bp fragment containing the filamentous bacteriophage f1 double strand origin of replication flanking the insert of interest was constructed (FIG. 3). The vector is based on a colE1 (pUC) replicon and confers ampicillin resistance. It does not contain a single strand origin or a packaging signal for packaging by f1 helper phages. As a test insert the β-galactosidase gene of pCH110 was inserted between the LoxP site and the f1-DS origin since its presence can be easily monitored by the appearance of blue colonies in the presence of the chromogenic substrate X-gal.

The 46 bp constituting the f1 double-stranded origin of replication (5'-CGTCGACCTCGA<u>TTGTTCCAGTTTG GAACAAGAGTCCACTATTAAAGAACGTGGACTCGT</u>ACCC-3' [SEQ ID NO: 21]; the double-stranded origin is underlined; the incised strand is complementary to the sequence shown)was inserted as a synthetic 46 bps oligomer between the KpnI and XhoI sites of pBC SK$^+$ (FIG. 6, SEQ ID NO: 1). The wild type LoxP site (5'-CGAATTGGAGCT<u>ATAACTTCGTATAATGTATGCTATACGAAGTTATC</u> A T ATGGCGGTGGCGGCCGCTCTAGAAC-3' [SEQ ID NO: 16]; the LoxP site is underlined) was inserted as a 34 bps oligomer between the SacI and SacII sites of pBC SK$^+$. A plasmid containing both elements was generated by combining the appropriate ScaI-EcoRI fragments. The resulting cassette containing the LoxP and f1 double-stranded origin inserted into the polylinker was then transferred as a BssHII fragment to the BluescriptII SK$^+$ from which the function elements of the f1 origin located between nucleotides 90 and 583 has been deleted by PCR. Finally, the β-gal gene was inserted as a BamHI-SalI fragment from pCH110 (Pharmacia Biotech) between the BamHI and HindIII sites.

Second Vector Construction

The second vector contains the same LoxP sites and f1 double strand origin of replication as the first vector. The second vector also contains the same origin of replication as the first vector but confers chloramphenicol resistance In addition, the f1 single strand origin of replication and the f1 packaging signal was included in the vector backbone matching the f1 double strand origin in orientation. The *E. coli* rpsL gene was inserted between the LoxP site and the f1 double strand origin of replication. Expression of the wild type rpsL gene confers streptomycin sensitivity to a streptomycin resistant host strain containing a mutation of the rpsL gene and can thus be selected against.

The 46 bp constituting the f1 double-stranded origin of replication was inserted as a synthetic 46 bps oligomer between the KpnI and XhoI cites of pBC SK$^+$. The wild type LoxP site was inserted as a 34 bps oligomer between the SacI and SacII sites of pBC SK$^+$. A plasmid containing both elements was generated by combining the appropriate ScaI-EcoRI fragments. Into this vector the wild type *E. coli* rpsL gene was inserted as a PCR amplified fragment from *E. coli* K12 (nt 7890-7421 of GenBank Accession No AE00410) between the EcoRI and HindIII sites. The EcoRI and HindIII restriction sites were added to the primer used for amplification of the rpsL gene. The resulting cassette containing the LoxP, wild type rpsL gene and f1 double-stranded origin was then transferred as a BssHII fragment to the BssHII digested pBC KS$^+$ from which the f1 double-stranded origin containing sequences located between nucleotides 135 and 178 had been deleted by PCR.

Recombination and Rescue

A co-integrate vector comprising the first vector and the second vector was formed by site-specific recombination using Cre-recombinase. This was achieved by mixing 100 ng of each vector with 1 µg of Cre-recombinase (Stratagene, La Jolla, Calif.) in 10 µl of 50 mM Tris HCL pH 7.5, 10 mM MgCl$_2$ and 30 mM NaCl and subsequent incubation at 37° C. for 45 minutes. The reaction was stopped by heat-inactivation for 15 minutes at 65° C.

To rescue the product vector from the co-integrate vector, chemically competent XL1-blue or XL10 gold (kanR) (both strains from Stratagene, LaJolla, Calif.) were transformed with the above recombination reaction. Either strain has high transformation efficiencies and carries the F' plasmid required to render the host injectable by filamentous phages such as f1. Transformation was performed by mixing 2.5 µl of the recombination reaction with 100 µl of competent cells, incubation on ice for 20 minutes and subsequent hear shock at 42° C. for 45 seconds. After the heat shock, 1 ml of 1×NZY, 10 µl of Exassist helper phage (10$^8$ pfu; Stratagene, LaJolla, Calif.) and 100 µl of a fresh stationary culture of XLOLR-S$^R$ were added and incubated for 2 hours at 37° C. while shaking. The XLOLR-S$^R$ strain serves as the secondary host. The secondary host can be selected for with Streptomycin. Exassist is used as a helper phage allowing packaging of the rescued single-stranded product vector. The helper phage is replication competent in the primary host (XL1-blue or XL10 gold) which contains the suppressor mutation supE but not in the secondary host (XLOLR-S$^R$) that contains no suppressor mutations. The rescued product plasmid was selected for by plating 100 or 200 µl on LB plates supplemented with Chloramphenicol (34 µg/ml), Streptomycin (75 µg/ml) and X-gal. Successful insert transfer should result in chloramphenicol resistant colonies expressing b-galactosidase activity, evidenced by formation of blue colonies on X-gal containing plates.

cell the first and second vectors described above, wherein the host cell expresses a site-specific recombinase which can catalyze the recombination of the first and second vectors, thus generating a co-integrate vector, and wherein the gene of interest may be rescued from the co-integrate vector by rolling circle replication.

First Vector Construction

In order to test the feasibility of insert transfer by the above method, a first vector containing a ΦC31 attP site and a 46 bp fragment containing the filamentous bacteriophage f1 double strand origin of replication flanking the insert of interest was constructed (FIG. 3). The vector is based on a colE1 (pUC) replicon and confers ampicillin resistance. It does not contain a single strand origin or a packaging signal for packaging by f1 helper phages. As a test insert the β-galactosidase gene of pCH110 was inserted between the ΦC31 attP site and the f1-DS origin since its presence can be easily monitored by the appearance of blue colonies in the presence of the chromogenic substrate X-gal.

The 46 bp constituting the f1 double-stranded origin of replication (5'-CGTCGACCTCGA<u>TTGTTCCAGTTTG GAACAAGAGTCCACTATTAAAGAACGTGGACTCGT</u> ACCC-3' [SEQ ID NO: 21]; the double-stranded origin is underlined; the incised strand is complementary to the sequence shown) was inserted as a synthetic 46 bps oligomer between the KpnI and XhoI sites of pBC SK$^+$ (SEQ ID NO:1). The ΦC31 attP site was inserted between the SacI and SacII sites of pBC SK$^+$. A plasmid containing both elements was generated by combining the appropriate ScaI-EcoRI fragments. The resulting cassette containing the attP site and f1 double-stranded origin inserted into the polylinker was then transferred as a BssHII fragment to the BluescriptII SK$^+$ from which the function elements of the f1

TABLE 1

Transfer of β-gal from a first vector to a product vector

| Input | Colony Count$^a$ | Transfer Efficiency$^b$ (colonies/µg target plasmid) | Transfer Error Rate (white colonies/total colonies) |
|---|---|---|---|
| first vector-βgal | expt. 1$^c$ | — | N/A |
|  | expt. 2$^d$ | — | N/A |
| second vector | expt. 11 (1 w) | 2 × 10$^7$ | N/A |
|  | expt. 217 (17 w) | 3.4 × 10$^2$ | N/A |
| first vector-βgal + second vector | expt. 1488 (0 w) | 1.2 × 10$^4$ | <2 × 10$^{-3}$ (<0.2%) |
|  | expt. 24.1 × 10$^3$ (6 w) | 8.2 × 10$^5$ | 1.4 × 10$^{-3}$ (0.146%) |

$^a$200 µl of 1.1 ml transformation mix plated
$^b$the transfer efficiency is dependent on the concentration of either reaction partner and has been arbitrarily referred to the second vector
$^c$XL1 blue has been used as primary host in experiment 1
$^d$XL10 gold (kan$^R$) has been used as primary host in experiment 2

Results of the transfer experiment described above are shown in table 1. Plasmid DNA of 18 blue colonies were analyzed by restriction digestion. All vectors displayed the restriction pattern expected for successful transfer. All white colonies analyzed by restriction digestion were indistinguishable from the second vector and presumably resulted form mutations in the rpsL insert serving as the negative selectable marker. The differences in the transfer efficiency between experiment 1 and experiment 2 is probably due to the different transformation efficiencies of the primary hosts used.

EXAMPLE 2

In an alternative embodiment the present invention provides a method of transfer of a gene of interest from a first vector to a product vector comprising introducing to a host origin located between nucleotides 90 and 583 has been deleted by PCR. Finally, the β-gal gene was inserted as a BamHI-SalI fragment from pCH110 (Pharmacia Biotech) between the BamHI and HindIII sites.

Second Vector Construction

The second vector contains a ΦC31 attB site and f1 double strand origin of replication as the first vector. The second vector also contains the same origin of replication as the first vector but confers chloramphenicol resistance In addition, the f1 single strand origin of replication and the f1 packaging signal was included in the vector backbone matching the f1 double strand origin in orientation. The *E. coli* rpsL gene was inserted between the ΦC31 attB site and the f1 double strand origin of replication. Expression of the wild type rpsL gene confers streptomycin sensitivity to a streptomycin resistant host strain containing a mutation of the rpsL gene and can thus be selected against.

The 46 bp constituting the f1 double-stranded origin of replication was inserted as a synthetic 46 bps oligomer between the KpnI and XhoI cites of pBC SK+. The ΦC31 attB site was inserted between the SacI and SacII sites of pBC SK+. A plasmid containing both elements was generated by combining the appropriate ScaI-EcoRI fragments. Into this vector the wild type *E. coli* rpsL gene was inserted as a PCR amplified fragment from *E. coli* K12 (nt 7890-7421 of GeneBank Accession No AE00410) between the EcoRI and HindIII sites. The EcoRI and HindIII restriction sites were added to the primer used for amplification of the rpsL gene. The resulting cassette containing the attB site, wild type rpsL gene and f1 double-stranded origin was then transferred as a BssHII fragment to the BssHII digested pBC KS+ from which the f1 double-stranded origin containing sequences located between nucleotides 135 and 178 had been deleted by PCR.

In Vivo Recombination

To generate the co-integrate vector, the first and second vectors are co-transformed into *E. coli*. with plasmid pInt (Groth et al., 2000, *Proc Natl Acad Sci USA*, 97:5995) from which ΦC31 integrase is expressed, thus supporting the recombination of plasmid vectors bearing attP/B sites. Transformation is performed by mixing between 0.1 and 50 ng each of the first and second vectors with 100 μl of competent XL1-blue or XL10 gold cells comprising an integrase expression vector (comprising the ΦC31-integrase gene cloned into pGM4 containing a gentamycin resistance marker). The mixture is incubated on ice for 20 minutes and subsequently heat shocked at 42° C. for 45 seconds. After the heat shock, cells are incubated at 37° C. for 2–4 hours. Subsequently, 1 ml of NYZ, 10 μl of Exassist helper phage ($10^8$ pfu; Stratagene LaJolla, Calif.) and 100 μl of a fresh stationary culture of XLOLR-$S^R$ cells were added and incubated for 2 hours at 37° C. while shaking. The XLOLR-$S^R$ strain serves as the secondary host. The secondary host may be selected for with streptomycin, as the presence of the rpsL gene in the first, second and co-integrate vectors will confer streptomycin sensitivity to cell bearing these vectors, whereas secondary host cells bearing the product vector will be selected for. Exassist is used as a helper phage allowing packaging of the rescued single-stranded product vector. The rescued product plasmid is selected for by plating 100 to 200 μl on LB plates supplemented with chloramphenicol (34 μg/ml), streptomycin (75 μg/ml) and X-gal. Successful gene of interest transfer should result in chloramphenicol resistant colonies expressing β-galactosidase activity, evidenced by formation of blue colonies on X-gal containing plates.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A method of transfer of a gene of interest to a product vector comprising:

a) contacting in vitro:
  a first vector comprising:
    a gene of interest,
    a gene encoding a first selectable marker,
    a double-stranded origin of replication of a rolling circle replicon; and
    a site-specific recombination recognition site, wherein said gene of interest is interposed between said double-stranded origin of replication of a rolling circle replicon and said site-specific recombination recognition site;
  a second vector comprising:
    a gene encoding a negative selectable marker,
    a double-stranded origin of replication of a rolling circle replicon,
    a site-specific recombination recognition site,
    a single-stranded origin of replication, and
    a gene encoding a second selectable marker, wherein said negative selectable marker is interposed between said double-stranded origin of replication of a rolling circle replicon and said site-specific recombination recognition site; and
  a site-specific recombinase, wherein said contacting permits formation of a co-integrate vector comprising said first and said second vector;

b) introducing said co-integrate vector into a prokaryotic host cell so as to permit the formation of a product vector comprising (i) said gene of interest interposed between said double-stranded origin of replication of said second vector and said site-specific recombination recognition site, (ii) said single-stranded origin of replication of said second vector, and (iii) said gene encoding said second selectable marker, said product vector not including both of said negative selectable marker and said gene encoding said first selectable marker, and wherein said product vector is formed by rolling circle replication.

2. The method of claim 1, further comprising the step of isolating said product vector from said prokaryotic host cell.

3. The method of claim 1, wherein said first and second selectable markers are different.

4. The method of claim 1, wherein each of said site-specific recombinase recognition sites is selected from the group consisting of: loxP, loxP2, loxP3, loxP23, loxP511, loxB, loxC2, loxL, loxR, loxΔ86, loxΔ117, frt, dif, Km sites, λ-phage att sites, and ΦC31 att sites.

5. The method of claim 1, wherein each of said double-stranded origins of replication is the double-stranded origin of replication of the filamentous bacteriophage f1.

6. The method of claim 1, wherein each of said double-stranded origins of replication is the double-stranded origin of replication of the plasmid pKym.

7. The method of claim 1, wherein said gene encoding a negative selectable marker is one of rpsL and sacB.

8. The method of claim 1, wherein said gene encoding one of said first or second selectable marker, independently, is selected from the group consisting of: kanamycin resistance gene, the ampicillin resistance gene, the tetracycline resistance gene, the chloramphenicol resistance gene, the spectinomycin resistance gene, the gentamycin resistance gene and the streptomycin resistance gene.

\* \* \* \* \*

SEQUENCE LISTING

<160> NUMBER OF SEQ ID NOS: 21

<210> SEQ ID NO 1
<211> LENGTH: 3400
<212> TYPE: DNA
<213> ORGANISM: Unknown
<220> FEATURE:
<223> OTHER INFORMATION: Nucleotide sequence of plasmid pBC SK+

<400> SEQUENCE: 1

```
ctaaattgta agcgttaata ttttgttaaa attcgcgtta aatttttgtt aaatcagctc      60 atttttaac caataggccg aaatcggcaa atcccttat aaatcaaaag aatagaccga      120
gatagggttg agtgttgttc cagtttggaa caagagtcca ctattaaaga acgtggactc      180
caacgtcaaa gggcgaaaaa ccgtctatca gggcgatggc ccactacgtg aaccatcacc      240
ctaatcaagt tttttggggt cgaggtgccg taaagcacta aatcggaacc ctaaagggag      300
cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcgtaata cgactcacta tagggcgaat tgggtaccgg      660
gccccccctc gaggtcgacg gtatcgataa gcttgatatc gaattcctgc agcccggggg      720
atccactagt tctagagcgg ccgccaccgc ggtggagctc cagcttttgt tccctttagt      780
gagggttaat tgcgcgcttg gcgtaatcat ggtcatagct gtttcctgtg tgaaattgtt      840
```

```
atccgctcac aattccacac aacatacgag ccggaagcat aaagtgtaaa gcctggggtg      900
cctaatgagt gagctaactc acattaattg cgttgcgctc actgcccgct ttccagtcgg      960
gaaacctgtc gtgccagctg cattaatgaa tcggccaacg cgcggggaga ggcggtttgc     1020
gtattgggcg ctcttccgct tcctcgctca ctgactcgct gcgctcggtc gttcggctgc     1080
ggcgagcggt atcagctcac tcaaaggcgg taatacggtt atccacagaa tcaggggata     1140
acgcaggaaa gaacatgtga gcaaaaggcc agcaaaaggc caggaaccgt aaaaaggccg     1200
cgttgctggc gtttttccat aggctccgcc ccctgacga gcatcacaaa aatcgacgct     1260
caagtcagag gtggcgaaac ccgacaggac tataaagata ccaggcgttt ccccctggaa     1320
gctccctcgt gcgctctcct gttccgaccc tgccgcttac cggatacctg tccgcctttc     1380
tcccttcggg aagcgtggcg ctttctcata gctcacgctg taggtatctc agttcggtgt     1440
aggtcgttcg ctccaagctg ggctgtgtgc acgaaccccc cgttcagccc gaccgctgcg     1500
ccttatccgg taactatcgt cttgagtcca acccggtaag acacgactta tcgccactgg     1560
cagcagccac tggtaacagg attagcagag cgaggtatgt aggcggtgct acagagttct     1620
tgaagtggtg gcctaactac ggctacacta aaggacagt atttggtatc tgcgctctgc     1680
tgaagccagt taccttcgga aaagagttg gtagctcttg atccggcaaa caaaccaccg     1740
ctggtagcgg tggtttttt gtttgcaagc agcagattac gcgcagaaaa aaaggatctc     1800
aagaagatcc tttgatcttt tctacggggt ctgacgctca gtggaacgaa aactcacgtt     1860
aagggatttt ggtcatgaga ttatcaaaaa ggatcttcac ctagatcctt ttcgaccgaa     1920
taaatacctg tgacggaaga tcacttcgca gaataaataa atcctggtgt ccctgttgat     1980
accgggaagc cctgggccaa ctttttggcga aaatgagacg ttgatcggca cgtaagaggt     2040
tccaactttc accataatga aataagatca ctaccgggcg tatttttga gttgtcgaga     2100
ttttcaggag ctaaggaagc taaaatggag aaaaaaatca ctggatatac caccgttgat     2160
atatcccaat ggcatcgtaa agaacatttt gaggcatttc agtcagttgc tcaatgtacc     2220
tataaccaga ccgttcagct ggatattacg gcctttttaa agaccgtaaa gaaaataag     2280
cacaagtttt atccggcctt tattcacatt cttgcccgcc tgatgaatgc tcatccggaa     2340
ttacgtatgg caatgaaaga cggtgagctg gtgatatggg atagtgttca cccttgttac     2400
accgttttcc atgagcaaac tgaaacgttt tcatcgctct ggagtgaata ccacgacgat     2460
ttccggcagt ttctacacat atattcgcaa gatgtggcgt gttacggtga aaacctggcc     2520
tatttcccta aagggtttat tgagaatatg ttttcgtct cagccaatcc ctgggtgagt     2580
ttcaccagtt ttgattaaa cgtggccaat atggacaact tcttcgcccc cgttttcacc     2640
atgggcaaat attatacgca aggcgacaag gtgctgatgc cgctggcgat tcaggttcat     2700
catgccgttt gtgatggctt ccatgtcggc agaatgctta atgaattaca acagtactgc     2760
gatgagtggc agggcgggc gtaattttt taaggcagtt attggtgccc ttaaacgcct     2820
ggttgctacg cctgaataag tgataataag cggatgaatg gcagaaattc gaaagcaaat     2880
tcgacccggt cgtcggttca gggcagggtc gttaaatagc cgcttatgtc tattgctggt     2940
ttaccggttt attgactacc ggaagcagtg tgaccgtgtg cttctcaaat gcctgaggcc     3000
agtttgctca ggctctcccc gtggaggtaa taattgacga tatgatcctt ttttctgat     3060
caaaagtgct catcattgga aaacgttctt cggggcgaaa actctcaagg atcttaccgc     3120
tgttgagatc cagttcgatg taacccactc gtgcacccaa ctgatcttca gcatctttta     3180
ctttcaccag cgtttctggg tgagcaaaaa caggaaggca aaatgccgca aaaaagggaa     3240
```

```
taagggcgac acggaaatgt tgaatactca tactcttcct ttttcaatat tattgaagca    3300
tttatcaagg gttattgtct catgagcgga tacatatttg aatgtattta gaaaaataaa    3360
caaatagggg ttccgcgcac atttccccga aaagtgccac                          3400

<210> SEQ ID NO 2
<211> LENGTH: 30
<212> TYPE: DNA
<213> ORGANISM: Bacteriophage phi-X174

<400> SEQUENCE: 2
caacttgata ttaataacac tatagaccac                                     30

<210> SEQ ID NO 3
<211> LENGTH: 46
<212> TYPE: DNA
<213> ORGANISM: Bacteriophage f1

<400> SEQUENCE: 3
gagtccacgt tctttaatag tggactcttg ttccaaactg gaacaa                   46

<210> SEQ ID NO 4
<211> LENGTH: 42
<212> TYPE: DNA
<213> ORGANISM: Shigella sonnei

<400> SEQUENCE: 4
ttgtatttat acttaaggga taaatggcgg atatgaaata gt                       42

<210> SEQ ID NO 5
<211> LENGTH: 29
<212> TYPE: DNA
<213> ORGANISM: Unknown
<220> FEATURE:
<223> OTHER INFORMATION: Double stranded origin of replication of
      plasmid pA

<400> SEQUENCE: 5
caggtatgcg gaaaacttta ggaacaagg                                      29

<210> SEQ ID NO 6
<211> LENGTH: 35
<212> TYPE: DNA
<213> ORGANISM: Unknown
<220> FEATURE:
<223> OTHER INFORMATION: Double stranded origin of replication for
      plasmid pBL

<400> SEQUENCE: 6
acttatcttg ataataaggg taactattta cggcg                               35

<210> SEQ ID NO 7
<211> LENGTH: 21
<212> TYPE: DNA
<213> ORGANISM: Unknown
<220> FEATURE:
<223> OTHER INFORMATION: Double stranded origin of replication from
      plasmid pSSU1

<400> SEQUENCE: 7
gggggcgtac tacgaccccc c                                              21

<210> SEQ ID NO 8
<211> LENGTH: 119
```

```
<212> TYPE: DNA
<213> ORGANISM: Unknown
<220> FEATURE:
<223> OTHER INFORMATION: Double stranded origin of replication from
      plasmid p1414

<400> SEQUENCE: 8
gttttaaaaa agccggctgt tttcagccgg cttttttcg attttggcgg gggtcttttc      60
ttatcttgat actatataga aacaccaaga ttttttaaaa gccttgcgtg tcaaggctt    119

<210> SEQ ID NO 9
<211> LENGTH: 71
<212> TYPE: DNA
<213> ORGANISM: Unknown
<220> FEATURE:
<223> OTHER INFORMATION: Double stranded origin of replication from
      plasmid pDC123

<400> SEQUENCE: 9
tttctccgaa aaatctaaa atatgggggg gctactacga ccccccctat gccaaaatca     60 aaaaaaaac g                                                          71

<210> SEQ ID NO 10
<211> LENGTH: 100
<212> TYPE: DNA
<213> ORGANISM: Unknown
<220> FEATURE:
<223> OTHER INFORMATION: Single stranded origin of replication from
      plasmid pA

<400> SEQUENCE: 10
aacaagggtt gttcgcgggg acaaaactag ccccaagctc gcgtttccgc cgttagtacc     60
ttgacgcggc tttacccagc gcgcctacgc gccgagattt                          100

<210> SEQ ID NO 11
<211> LENGTH: 200
<212> TYPE: DNA
<213> ORGANISM: Unknown
<220> FEATURE:
<223> OTHER INFORMATION: Single stranded origin of replication from
      plasmid pPL

<400> SEQUENCE: 11
gtcaacgata agcggacttc ggcgttagcc gatggagcat taaggagttg atggtttcca     60
ggctcttggc gacagcaaaa aggaaaaaca cttttttccct tcctcgacag agccaccgga   120
cctagaaaga aagttttttgg ctgccccttt gggcggtctt tttttggcca tgcggagcat   180
ggctcggcgg agccgacggc                                                200

<210> SEQ ID NO 12
<211> LENGTH: 125
<212> TYPE: DNA
<213> ORGANISM: Unknown
<220> FEATURE:
<223> OTHER INFORMATION: Single stranded origin of replication from
      plasmid pSSU1

<400> SEQUENCE: 12 gcgattttatg ccgagaaaac tcttgctagg aagctatgcg aaatagacta agtcgacagg    60
ctgaaagctt gccgaccgaa cacgacagtc agatttcagc tcctagcaag aggaaattgg   120
aataa                                                               125
```

<210> SEQ ID NO 13
<211> LENGTH: 150
<212> TYPE: DNA
<213> ORGANISM: Unknown
<220> FEATURE:
<223> OTHER INFORMATION: Single stranded origin of replication from
      plasmid p1414

<400> SEQUENCE: 13
tgggggtgag tcaacggtaa ccggaccgta gggaggatta aggagttgac ccacccgaac     60
cctttcagca ctcaaacaaa cccgtttgtt tgacgccaac gccccccgaa gatgcggggg    120
gttgggggga ttgaatgctg gcatccaacg                                     150

<210> SEQ ID NO 14
<211> LENGTH: 101
<212> TYPE: DNA
<213> ORGANISM: Unknown
<220> FEATURE:
<223> OTHER INFORMATION: Single stranded origin of replication from
      plasmid pDC123

<400> SEQUENCE: 14
tatttgacaa caagtaacca agtgactgcc gtcctttgtc cgtgtccgtc cagcctttcg     60
gctcggcacg tcctagcgta ctctgtcact gcttattgtc a                        101

<210> SEQ ID NO 15
<211> LENGTH: 120
<212> TYPE: DNA
<213> ORGANISM: Bacteriophage f1

<400> SEQUENCE: 15
aaaaaccgtc tacagggcga tggcccacta cgtgaaccat caccctaatc aagttttttg     60
gggtcgaggt gccgtaaagc actaaatcgg aaccctaaag ggagccccccg atttagagct   120

<210> SEQ ID NO 16
<211> LENGTH: 74
<212> TYPE: DNA
<213> ORGANISM: Unknown
<220> FEATURE:
<223> OTHER INFORMATION: Sequence encoding loxP site

<400> SEQUENCE: 16
cgaattggag ctataacttc gtataatgta tgctatacga agttatcata tggcggtggc     60
ggccgctcta gaac                                                      74

<210> SEQ ID NO 17
<211> LENGTH: 34
<212> TYPE: DNA
<213> ORGANISM: Unknown
<220> FEATURE:
<223> OTHER INFORMATION: Variant lox site loxP511

<400> SEQUENCE: 17
ataacttcgt atagtataca ttatacgaag ttat                                34

<210> SEQ ID NO 18
<211> LENGTH: 34
<212> TYPE: DNA
<213> ORGANISM: Unknown
<220> FEATURE:
<223> OTHER INFORMATION: Variant lox site loxC2

<400> SEQUENCE: 18

-continued

```
acaacttcgt ataatgtatg ctatacgaag ttat                              34

<210> SEQ ID NO 19
<211> LENGTH: 34
<212> TYPE: DNA
<213> ORGANISM: Saccharomyces cerevisiae

<400> SEQUENCE: 19
gaagttccta ttctctagaa agtataggaa cttc                              34

<210> SEQ ID NO 20
<211> LENGTH: 290
<212> TYPE: DNA
<213> ORGANISM: Escherichia coli

<400> SEQUENCE: 20
aggctcaaca ggttggtggt tctcaccacc aaaagcacca cacccacgc aaaaacaagt    60 ttttgctgat ttttctttat aaatagagtg ttatgaaaaa ttagtttctc ttactctctt  120
tatgatattt aaaaaagcgg tgtcggcgcg gctacaacaa cgcgccgaca ccgttttgta  180
ggggtggtac tgactatttt tataaaaaac attattttat attagggtg ctgctagcgg   240 cgcggtgtgt tttttatag gataccgcta ggggcgctgc tagcggtgcg              290

<210> SEQ ID NO 21
<211> LENGTH: 64
<212> TYPE: DNA
<213> ORGANISM: Bacteriophage f1

<400> SEQUENCE: 21
cgtcgacctc gattgttcca gtttggaaca agagtccact attaaagaac gtggactcgt   60
accc                                                                64
```